(12) United States Patent
Lu et al.

(10) Patent No.: US 10,493,179 B2
(45) Date of Patent: Dec. 3, 2019

(54) MODIFIED SILK FILMS CONTAINING GLYCEROL

(71) Applicant: Trustees of Tufts College, Medford, MA (US)

(72) Inventors: Shenzhou Lu, Suzhou (CN); Xiaoqin Wang, Winchester, MA (US); Fiorenzo Omenetto, Lexington, MA (US); David L. Kaplan, Concord, MA (US)

(73) Assignee: Trustees of Tufts College, Medford, MA (US)

(*) Notice: Subject to any disclaimer, the term of this patent is extended or adjusted under 35 U.S.C. 154(b) by 0 days.

(21) Appl. No.: 14/755,215

(22) Filed: Jun. 30, 2015

(65) Prior Publication Data

US 2016/0038637 A1 Feb. 11, 2016

Related U.S. Application Data

(63) Continuation of application No. 13/122,837, filed as application No. PCT/US2009/060135 on Oct. 9, 2009, now abandoned.

(60) Provisional application No. 61/104,135, filed on Oct. 9, 2008.

(51) Int. Cl.

| | |
|---|---|
| *A61L 27/36* | (2006.01) |
| *A61L 27/38* | (2006.01) |
| *A61L 27/50* | (2006.01) |
| *C08J 3/18* | (2006.01) |
| *C08J 5/18* | (2006.01) |
| *C12N 11/02* | (2006.01) |
| *A61L 27/54* | (2006.01) |
| *B05D 1/30* | (2006.01) |
| *B05D 3/02* | (2006.01) |
| *B05D 3/10* | (2006.01) |
| *C08K 5/053* | (2006.01) |

(52) U.S. Cl.

CPC ....... *A61L 27/3604* (2013.01); *A61L 27/3804* (2013.01); *A61L 27/50* (2013.01); *A61L 27/54* (2013.01); *B05D 1/30* (2013.01); *B05D 3/0254* (2013.01); *B05D 3/107* (2013.01); *C08J 3/18* (2013.01); *C08J 5/18* (2013.01); *C08K 5/053* (2013.01); *C12N 11/02* (2013.01); *A61L 2420/06* (2013.01); *C08J 2389/00* (2013.01)

(58) Field of Classification Search

CPC ..... C08L 89/00; C08K 5/053; A61L 27/3604; A61L 27/3804; A61L 27/50; C12N 11/02
USPC .................. 424/94.1, 93.6, 93.7, 130.1, 400; 435/395; 514/1.1, 44 R, 773; 530/353

See application file for complete search history.

(56) References Cited

U.S. PATENT DOCUMENTS

| | | |
|---|---|---|
| 1,989,005 A | 1/1935 | Fink et al. |
| 3,755,560 A | 8/1973 | Dickert et al. |
| 3,929,678 A | 12/1975 | Laughlin et al. |
| 4,076,663 A | 2/1978 | Masuda et al. |
| 4,152,416 A | 5/1979 | Spitzer et al. |
| 4,233,212 A | 11/1980 | Otoi et al. |
| 4,421,769 A | 12/1983 | Dixon et al. |
| 4,820,418 A | 4/1989 | Hirotsu et al. |
| 4,838,965 A | 6/1989 | Bussard |
| 4,937,370 A | 6/1990 | Sabatelli |
| 4,999,186 A | 3/1991 | Sabatelli et al. |
| 5,011,681 A | 4/1991 | Ciotti et al. |
| 5,047,507 A | 9/1991 | Buchegger et al. |
| 5,073,371 A | 12/1991 | Turner et al. |
| 5,073,372 A | 12/1991 | Turner et al. |
| 5,087,372 A | 2/1992 | Toyomoto et al. |
| 5,245,012 A | 9/1993 | Lombari et al. |
| 5,290,494 A | 3/1994 | Coombes et al. |
| 5,591,828 A | 1/1997 | Bosslet et al. |
| 5,606,019 A | 2/1997 | Cappello |
| 5,728,810 A | 3/1998 | Lewis et al. |
| 5,770,193 A | 6/1998 | Vacanti et al. |
| 5,827,508 A | 10/1998 | Tanner et al. |
| 5,935,556 A | 8/1999 | Tanner et al. |
| 5,968,485 A | 10/1999 | Robinson |
| 5,972,316 A | 10/1999 | Robinson |
| 5,994,099 A | 11/1999 | Lewis et al. |
| 6,110,590 A | 8/2000 | Zarkoob et al. |
| 6,123,819 A | 9/2000 | Peeters |
| 6,175,053 B1 | 1/2001 | Tsubouchi |
| 6,287,340 B1 | 9/2001 | Altman et al. |
| 6,592,623 B1 | 7/2003 | Bowlin et al. |
| 6,815,427 B2 | 11/2004 | Tsubouchi et al. |

(Continued)

FOREIGN PATENT DOCUMENTS

| | | |
|---|---|---|
| CA | 2405850 A1 | 10/2002 |
| CN | 1348820 A | 5/2002 |

(Continued)

OTHER PUBLICATIONS

Agarwal, et al., Effect of Moisture Absorption on the Thermal Properties of Bombyx mori Silk Fibroin Films, Journal of Applied Polymer Science, 63(3):401-410 (1997).

(Continued)

*Primary Examiner* — Janet L Epps-Smith
(74) *Attorney, Agent, or Firm* — Quarles & Brady LLP; Jessica L. Lewis

(57) ABSTRACT

The present invention provides for compositions and methods for preparing aqueous insoluble, ductile, flexible silk fibroin films. The silk films comprise silk fibroin and about 10% to about 50% (w/w) glycerol, and are prepared by entirely aqueous processes. The ductile silk film may be further treated by extracting the glycerol from and re-drying the silk film. Active agents may be embedded in or deposited on the glycerol modified silk film for a variety of medical applications. The films may be shaped into 3-dimensional structures, or placed on support surfaces as labels or coatings. The glycerol modified silk films of the present invention are useful in variety of applications such as tissue engineering, medical devices or implants, drug delivery, and edible pharmaceutical or food labels.

14 Claims, 9 Drawing Sheets

(56) References Cited

U.S. PATENT DOCUMENTS

| | | |
|---|---|---|
| 6,902,932 B2 | 6/2005 | Altman et al. |
| 7,041,797 B2 | 5/2006 | Vollrath |
| 7,057,023 B2 | 6/2006 | Islam et al. |
| 7,285,637 B2 | 10/2007 | Armato et al. |
| 7,297,678 B2 | 11/2007 | Kumar et al. |
| 7,635,755 B2 | 12/2009 | Kaplan et al. |
| 7,662,409 B2 | 2/2010 | Masters |
| 7,674,882 B2 | 3/2010 | Kaplan et al. |
| 7,727,575 B2 | 6/2010 | Kaplan et al. |
| 7,842,780 B2 | 11/2010 | Kaplan et al. |
| 7,901,668 B2 | 3/2011 | Tsubouchi et al. |
| 7,960,509 B2 | 6/2011 | Kaplan et al. |
| 8,071,722 B2 | 12/2011 | Kaplan et al. |
| 2002/0028243 A1 | 3/2002 | Masters |
| 2003/0007991 A1 | 1/2003 | Masters |
| 2003/0165548 A1 | 9/2003 | Tsubouchi et al. |
| 2003/0183978 A1 | 10/2003 | Asakura |
| 2004/0005363 A1 | 1/2004 | Tsukada et al. |
| 2004/0266992 A1 | 12/2004 | Migliaresi et al. |
| 2007/0212730 A1 | 9/2007 | Vepari et al. |
| 2008/0085272 A1 | 4/2008 | Kaplan et al. |
| 2008/0293919 A1 | 11/2008 | Kaplan et al. |
| 2009/0202614 A1 | 8/2009 | Kaplan et al. |
| 2009/0232963 A1 | 9/2009 | Kaplan et al. |
| 2009/0234026 A1 | 9/2009 | Kaplan et al. |
| 2010/0028451 A1 | 2/2010 | Kaplan et al. |
| 2010/0046902 A1 | 2/2010 | Kaplan et al. |
| 2010/0055438 A1 | 3/2010 | Kaplan et al. |
| 2010/0063404 A1 | 3/2010 | Kaplan et al. |
| 2010/0065784 A1 | 3/2010 | Kaplan et al. |
| 2010/0068740 A1 | 3/2010 | Kaplan et al. |
| 2010/0070068 A1 | 3/2010 | Kaplan et al. |
| 2010/0096763 A1 | 4/2010 | Kaplan et al. |
| 2010/0120116 A1 | 5/2010 | Kaplan et al. |
| 2010/0178304 A1 | 7/2010 | Wang et al. |
| 2010/0191328 A1 | 7/2010 | Kaplan et al. |
| 2010/0196447 A1 | 8/2010 | Kaplan et al. |
| 2011/0008406 A1 | 1/2011 | Altman et al. |
| 2011/0046686 A1 | 2/2011 | Kaplan et al. |
| 2011/0076384 A1 | 3/2011 | Cannizzaro et al. |
| 2011/0111031 A1* | 5/2011 | Jiang .................. A61K 9/0024 424/484 |
| 2011/0135697 A1 | 6/2011 | Omenetto et al. |
| 2011/0152214 A1 | 6/2011 | Boison et al. |
| 2011/0171239 A1 | 7/2011 | Kaplan et al. |
| 2011/0189292 A1 | 8/2011 | Lebreton et al. |
| 2011/0223153 A1 | 9/2011 | Lu et al. |
| 2012/0121820 A1 | 5/2012 | Kaplan et al. |
| 2012/0123519 A1 | 5/2012 | Lovett et al. |
| 2015/0079012 A1 | 3/2015 | Bellas et al. |

FOREIGN PATENT DOCUMENTS

| | | | |
|---|---|---|---|
| CN | 1732022 A | 2/2006 | |
| CN | 101234213 A | 8/2008 | |
| EP | 0404097 A2 | 12/1990 | |
| EP | 1440088 A2 | 7/2004 | |
| GB | 1182153 A | 2/1970 | |
| JP | 55-139427 | 10/1980 | |
| JP | S56-166235 A | 12/1981 | |
| JP | 60-142259 A | 7/1985 | |
| JP | 60-259677 | 12/1985 | |
| JP | 01118544 | 11/1989 | |
| JP | H05-39368 A | 2/1993 | |
| JP | H06-346314 | 12/1994 | |
| JP | H08-60547 A | 3/1996 | |
| JP | 08-295697 | 11/1996 | |
| JP | 10-36676 | 2/1998 | |
| JP | H10-251299 A | 9/1998 | |
| JP | 2000-273264 A | 10/2000 | |
| JP | 2002186847 A | 7/2002 | |
| JP | 2003-192807 A | 7/2003 | |
| JP | 2004-068161 A | 3/2004 | |
| JP | 2005-510268 A | 4/2005 | |
| JP | 2006-155653 A | 6/2006 | |
| JP | 2008-502739 A | 1/2008 | |
| JP | 05-043600 | 10/2012 | |
| JP | 05-043600 B2 | 10/2012 | |
| KR | 100431659 B1 | 5/2004 | |
| WO | WO-93/11161 A1 | 6/1993 | |
| WO | WO-1997/008315 A1 | 3/1997 | |
| WO | WO-98/22085 A1 | 5/1998 | |
| WO | WO-1999/001089 A1 | 1/1999 | |
| WO | WO-00/06110 A1 | 2/2000 | |
| WO | WO-00/24372 A1 | 5/2000 | |
| WO | WO-2001/036531 | 5/2001 | |
| WO | WO-01/056626 A1 | 8/2001 | |
| WO | WO-2002/072931 | 9/2002 | |
| WO | WO-03/022909 A1 | 3/2003 | |
| WO | WO-03/038033 A2 | 5/2003 | |
| WO | WO-04/000915 A2 | 12/2003 | |
| WO | WO-04/001103 A2 | 12/2003 | |
| WO | WO-04/041845 A2 | 5/2004 | |
| WO | WO-2004/060424 | 6/2004 | |
| WO | WO-04/062697 A2 | 7/2004 | |
| WO | WO-05/000483 A1 | 1/2005 | |
| WO | WO-2005/012606 A2 | 2/2005 | |
| WO | WO2005/103158 | 11/2005 | |
| WO | WO-2005/103158 | 11/2005 | |
| WO | WO-2005/123114 A2 | 12/2005 | |
| WO | WO-2006/042287 A2 | 4/2006 | |
| WO | WO-2006/076711 A2 | 7/2006 | |
| WO | WO-2007/016524 A2 | 2/2007 | |
| WO | WO-2007/098951 A2 | 9/2007 | |
| WO | WO-2007/103442 A1 | 9/2007 | |
| WO | WO-2008/085904 A1 | 7/2008 | |
| WO | WO-2008/106485 A2 | 9/2008 | |
| WO | WO-2008/108838 A2 | 9/2008 | |
| WO | WO-2008/118133 A2 | 10/2008 | |
| WO | WO-2008/118211 A2 | 10/2008 | |
| WO | WO-2008/127401 A2 | 10/2008 | |
| WO | WO-2008/127402 A2 | 10/2008 | |
| WO | WO-2008/127403 A2 | 10/2008 | |
| WO | WO-2008/127404 A2 | 10/2008 | |
| WO | WO-2008/127405 A2 | 10/2008 | |
| WO | WO-2008/140562 A2 | 11/2008 | |
| WO | WO-2008/150861 A1 | 12/2008 | |
| WO | WO-2009/061823 A1 | 5/2009 | |
| WO | WO-2009/100280 A2 | 8/2009 | |
| WO | WO-2009/126689 A2 | 10/2009 | |
| WO | WO-2009/140588 A1 | 11/2009 | |
| WO | WO-2009/155397 A2 | 12/2009 | |
| WO | WO 2009155397 A2 * | 12/2009 | .............. A61J 3/007 |
| WO | WO-2010/040129 A2 | 4/2010 | |
| WO | WO-2010/042798 A2 | 4/2010 | |
| WO | WO-2010/057142 A2 | 5/2010 | |
| WO | WO-2010/141133 A2 | 12/2010 | |
| WO | WO-2011/005381 A2 | 1/2011 | |
| WO | WO-2011/006133 A2 | 1/2011 | |
| WO | WO-2011/008842 A2 | 1/2011 | |
| WO | WO-2011/011347 A2 | 1/2011 | |
| WO | WO-2012/145739 A1 | 10/2012 | |
| WO | WO-2013/159101 A1 | 10/2013 | |

OTHER PUBLICATIONS

Altman, G. H. et al., Silk-based biomaterials, Biomaterials, 24:401-416 (2003).

Arai, T., et al., Preparation of Silk Fibroin and Polyallylamine Composites, Journal of Applied Polymer Sciences, 84: 1963-1970 (2002).

Asakura, T. et al., Conformational characterization of Bombyx mori silk fibroin in the solid state by high-frequency carbon-13 cross polarization-magic angle spinning NMR, x-ray diffraction, and infrared spectroscopy, Macromolecules, 18(10):1841-1845 (1985).

Asakura, T. et al., NMR of silk fibroin 2. 13C NMR study of the chain dynamics and solution structure of Bombyx mori silk fibroin, Macromolecules, 17:1075-1081 (1984).

Bettinger, C. et al., Silk Fibroin Microfluidic Devices, Adv. Mat., 19(19): 2847-2850 (2007).

(56) References Cited

OTHER PUBLICATIONS

Bini, E. et al., Mapping domain structures in silks from insects and spiders related to protein assembly, Journal of Molecular Biology, 335(1):27-40 (2004).
Canetti, M., et al., CD and small-angle x-ray scattering of silk fibroin in solution, Biopolymers, 28(9): 1613-1324 (1989).
Cao, China Doctor Dissertation, Full-text Database Medical and Health Science and Technology Series, 5:18-19 (2007).
Chen et al., pH sensitivity and ion sensitivity of hydrogels based on complex-forming chitosan/silk fibroin interpenetrating polymer network, J. Appl. Polymer Sci., 65:2257-62 (1997).
Chen et al., Research to the silk fibroin protein film modified by nano-TiO2, Acta Polymerica Sinica, 5: 649-653 (2006).
Chen et al., Separation of alcohol-water mixture by pervaporation through a novel natural polymer blend membrane-chitosan/silk fibroin blend membrane, J. Appl. Polymer Sci., 73:975-980 (1999).
Chen, J., et al., Human bone marrow stromal cell and ligament fibroblast responses on RGD-modified silk fibers, J. Biomed. Mater. Res. A. 67(2): 559-570 (2003).
Chen, X. et al., Conformation Transition Kinetics of Bombyx mori Silk Protein, Proteins: Structure, Function, and Bioinformatics, 68:223-231 (2007).
Chen, X. et al., Conformation transition kinetics of regenerated *Bombyx mori* silk fibroin membrane monitored by time-resolved FTIR spectroscopy, Biophysical Chemistry, 89:25-34 (2001).
Dai, L., et al., Effects of Glycerin on Structure Transition of PCA/SF Blends, Journal of Applied Polymer Science, 86: 2342-2347 (2002).
Database WPI Week 198205, Derwent Publications Ltd., London, GB; AN 1982-09092E & JP 56 166235 A, Abstract (Dec. 21, 1981).
Demura, M. et al., Immobilization of Biocatalysts with Bombyx mori Silk Fibroin by Several Kinds of Physical Treatment and Its Application to Glucose Sensors, Biosensors, 4(6):361-372 (1989).
Demura, M., Porous membrane of Bombyx mori silk fibroin: structure characterization, physical properties and application to glucose oxidase immobilization, Journal of Membrane Science, 59:32-52 (1991).
Derwent Record, Abstract of JP 08295697 A2, Production of Aqueous Solution of Silk Fibroin At High Concentration (Nov. 12, 1996).
Doshi et al., Electrospinning Process and Applications of Electrospun Fibers, J/Electrostatics, 35: 151-160 (1995).
Examination Report for EP 09 819 932.6, 4 pages (dated Apr. 8, 2014).
Freddi et al., Silk fibroin/cellulose blend films: preparation, structure, and physical properties, J Appl Polymer Sci, 56:1537-1545 (1995).
Gotoh, Y., et al., Physical Properties and Structure of poly(ethylene glycol)-silk fibroin Conjugate Films, Polymer, 38(2): 487-490 (1997).
Gupta et al., Patterned silk fimls from ionic liquid solubilized fibroin as scaffolds for cell growth, Langmuir, 23: 1315-1319 (2007).
Hijirida et al., 13C NMR of Nephila clavipes Marjo Ampullate Silk Gland, Biophysical Journal 71:3442-3447 (1996).
Hinman, M.B. et al., Synthetic spider silk: a modular fiber, Trends Biotechnol, 18(9):374-9 (2000).
Hofmann, S., et al., Silk fibroin as an organic polymer for controlled drug delivery, Journal of Controlled Release, 111:219-227 (2006).
Hu et al., Regulation of Silk Material Structure by Temperature-Controlled Water Vapor Annealing, Biomacraomolecules, 12:1686-1696 (2011).
Hu, X. et al., Dynamic Protein—Water Relationships during β-Sheet Formation, Macromolecules, 41:3939-3948 (2008).
Huang et al., Engineered collagen-PEO nanofibers and fabrics, J Biomater Sci Polymer Edn, 12(9):979-993 (2001).
Huang et al., Generation of Synthetic Elastin-Mimetic Small Diameter Fibers and Fiber Networks, Macromolecules, 33:2989-2997 (2000).
International Search Report of PCT/US09/60135, 3 pages (dated May 26, 2010).
Jin, H., et al., Biomaterial Films of Bombyx Mori Silk Fibroin with Poly(ethyiene oxide), Biomacromolecules, 5: 711-717 (2004).
Jin, H.J. and Kaplan, D.L., Mechanism of silk processing in insects and spiders, Nature 424(6952):1057-1061 (2003).
Jin, H.J. et al., Electrospinning Bombyx mori silk with poly(ethylene oxide), Biomacromolecules, 3(6):1233-9 (2002).
Jin, H.J. et al., Water-Stable Silk Films with Reduced 6-Sheet Content, Advanced Functional Materials, 15:1241-1247 (2005).
Jin,H-J et al., Electrospinning Bombyx mori Silk with Poly(ethylene oxide), Polymer Preprints (American Chemical Society, Division of Polymer Chemistry), 43(2):743-744 (2002).
Kaplan, et al., Silk, Protein Based Materials, 103-131 (1997).
Kawahara, Y., et al., Self-Expansion Behavior of Silk Fibroin Film, Macromolecular Materials and Engineering, 291: 458-462 (2006).
Kesenci, K., et al., Poly(epsilon-caprolactone-co-D,L-lactide) /silk fibroin composite materials: preparation and characterization, J.Biomater. Sci. Polymer Edn., 12(3): 337-351.
Kitagawa, T., et al., An analysis of Capilary Water Behavior in Poly-p-Phenylenebenzobisoxazole Fiber, Journal of Applied Polymer Science, 20: 1030-1036 (2001).
Kweon et al., Preparation of Semi-Interpreting Polymer Networks Composed of Silk Fibroin and Poly( ethylene glycol) Macromer, J. Appl. Polymer Sci., 80:1848-1853 (2001).
Lazaris, A. et al., Spider silk fibers spun from soluble recombinant silk produced in mammalian cells, Science. 295(5554):472-6 (2002).
Lee et al., Effect of Surface properties on the antithrombogeneicity of silk fibroin/S-carboxymethyl kerateine blend films, J. Biomater. Sci. Polymer Edn., 9(9): 905-914 (1998).
Liang, C. X., et al., Improvements of the physical properties of fibroin membranes with sodium alginate, J. Appl. Polymer Sci., 1937-1943 (1992).
Lu, Q. et al., Water-insoluble silk films with silk I structure, Acta Biomaterialia, 6(4):1380-1387 (2010).
Ma et al., Physical Properties of Silk Fibroin Films Treated with Various Plasticizers, J. Food Sci. Nutr., 10: 187-190 (2005).
Matsumoto, A., et al., Mechanisms of silk fibroin sol-gel transitions, J. Phys. Chem. B., 110(43): 21630-21638 (2006).
Megeed et al., Controlled Release of Plasmid DNA from a Genetically Engineered Silk-Elastin like Hydrogel, Pharmaceutical Research, 19(7):954-959 (2002).
Minoura, N. et al., Fine structure and oxygen permeability of silk fibroin membrane treated with methanol, Polymer, 31(2): 265-269 (1990).
Minoura, N., et al., Physico-chemical properties of silk fibroin membrane as a biomaterial, Biomats, 11: 430-434 (1990).
Motta, A. et al., Regenerated silk fibroin films: Thermal and dynamic mechanical analysis, Macromolecular Chemistry and Physics, 203(10-11):1658-1665 (2002).
Noishiki, Y., Mechanical Properties of Silk Fibroin-Microcrystalline Cellulose Composite Films, Journal of Applied Polymer Science, 86: 3425-3429 (2002).
Petrini, P. et al., Surface modification of polyurethane scaffolds with natural polymers: The use of silk fibroin, European Cells and Materials, 6(Supp.1): 30 (2003).
Reneker D.H. and Chun, I., Nanometre diameter fibres of polymer, produced by electrospinning, Nanotechnology, 7:216-223 (1996).
Sawyer et al., Dextran therapy in thrombophlebitis. Abstract, JAMA, 191(9):740-742 (1965).
Sofia et al. Functionalized Silk-Based Biomaterials for Bone Formation, J. Biomed. Mater. Res. 54:139-148 (2001).
Tsukada, M., et al., Structure and Compatibility of Poly(vinyl Alcohol)-Silk Fibroin (PVA/SF) Blend Films, Journal of Applied Polymer Science, Part B: Polymer Physics, 32: 243-248.
Valluzzi, R., et al., Orientation of silk III at the air-water interface, Int. J. Biol. Macromol., 24(2-3): 237-242 (1999).
Vepari, C. et al., Silk as a Biomaterial, Prog. Polym. Sci., 32(8-9): 991-1007 (2007).
Wang, X. et al., Biomaterial Coatings by Stepwise Deposition of Silk Fibroin, Langmuir, 21(24): 11335-11341 (2005).
Wang, X. et al., Silk microspheres for encapsulation and controlled release, Journal of Controlled Release, 117:360-370 (2007).
Wang, X., Controlled release from multilayer silk biomaterial coatings to modulate vascular cell responses, Biomaterials, 29(7): 894-903 (2008).

(56) References Cited

OTHER PUBLICATIONS

Wilson, D. L., Surface organization and nanopatterning of collagen by dip-pen nanolithography, PNAS 98(24): 13660-13664 (2001).
Written Opinion of PCT/US09/60135, 5 pages (dated May 26, 2010).
Yamada et al., AFM observation of silk fibroin on mica substrates: morphologies reflecting the secondary structure, Thin Solid Films, 440:208-16 (2003).
Zhang, YQ., Natural silk fibroin as a support for enzyme immobilization, Biotechnol. Adv., 16:961-971 (1998).
Zhou et al., Preparation of a novel core-shell nanostructured gold colloid-silk fibroin bioconjugate by the protein in situ redox technique at room temperature, Chern Commun, 2518-2519 (2001).
"Brittle" Merriam-Webster.com. 2017. https://www.merriam-webster.com (Jul. 7, 2011).
Acharya, C. et al., Performance evaluation of a silk protein-based matrix for the enzymatic conversion of tyrosine to L-DOPA, Biotechnology Journal, 3(2):226-233 (2008).
Batzer, M.A. et al., Enhanced evolutionary PCR using oligonucleotides with inosine at the 3'-terminus, Nucleic Acid Research, 19(18):5081 (1991).
Bayraktar, O. et al., Silk fibroin as a novel coating material for controlled release of theophylline, European Journal of Pharmaceutics and Biopharmaceutics, 60(3):373-381 (2005).
Carruthers, C.M. and Foster, P., Critical window of male reproductive tract development in rats following gestational exposure to di-n-butyl phthalate, Birth Defects Research Part B: Developmental and Reproductive Toxicology, 74:277-285 (2005).
Cavanagh, H.M. and Wilkinson, J.M., Biological activities of Lavender essential oil, Phytotherapy Research, 16(4):301-308 (2002).
Chothia, C. and Lesk, A.M., Canonical structures for the hypervariable regions of immunoglobulins, Journal of Molecular Biology, 196(4):901-917 (1987).
Collins, B.H. et al., Kiwifruit protects against oxidative DNA damage in human cells and in vitro, Nutrition and Cancer, 39(1):148-153 (2001).
Darbre, P.D. et al., Concentrations of parabens in human breast tumours, Journal of Applied Toxicology, 24(1):5-13 (2004).
Demura, M. and Asakura, T., Immobilization of glucose oxidase with Bombyx mori silk fibroin by only stretching treatment and its application to glucose sensor, Biotechnology and Bioengineering, 33(5):598-603 (1989).
Dikstein, S., Hydropharmacology, Cell Biochemistry and Function, 13:195-200 (1995).
Holliger, P. et al., "Diabodies": small bivalent and bispecific antibody fragments, Proceedings of the National Academy of Science, 90(14):6444-6448 (1993).
Hu, X, et al., Determining beta-sheet crystallinity in fibrous proteins by thermal analysis and infrared spectroscopy, Macromolecules, 39:6161-6170 (2006).
International Search Report for PCT/US2013/037613, 4 pages (dated Jul. 29, 2013).
Li, M. et al., Study on Porous Silk Fibroin Materials. II. Preparation and Characteristics of Spongy Porous Silk Fibroin Materials, Journal of Applied Polymer Science, 79:2192-2199 (2001).
Lu, S. et al., Insoluble and flexible silk films containing glycerol, Biomacromolecules, 11(1):143-50 (2010).
Lu, S. et al., Stabilization of enzymes in silk films, Biomacromolecules, 10(5):1032-1042 (2009).
Lucas, F. et al., The Silk Fibroins, Advances in Protein Chemistry, 13:107-242 (1958).
Min, S. et al., Preparation and Characterization of Crosslinked Porous Silk Fibroin Gel, Sen'l Gakkaishi: The Society of Fiber Science and Technology Japan, 54(2):85-92 (1998).
Miyrairi, et al., Properties of b-glucosidase immobilized in sericin membrane, Journal of Fermentation Technology, 56:303 (1978).
Murphy, A.R. et al., Modification of Silk Fibroin Using Diazonium Coupling Chemistry and the Effects on hMSC Proliferation and Differentiation, Biomaterials, 29(19):2829-2838 (2008).
Nazarov, R. et al., Porous 3-D scaffolds from regenerated silk fibroin, Biomacromolecules, 5(3):718-726 (2004).
Ohtsuka, E. et al., An alternative approach to deoxyoligonucleotides as hybridization probes by insertion of deoxyinosine at ambiguous codon positions, Journal of Biological Chemistry, 260:2605-2608 (1985).
Park, J.H. et al., The effect of heat on skin permeability, International Journal of Pharmacology, 359(1-2):94-103 (2008).
Perry, H. et al., Nano- and Micropatterning of Optically Transparent, Mechanically Robust, Biocompatible Sillk Fibroin Films, Advanced Materials, 20(16):3070-2 (2008).
Rossolini, G.M. et al., Use of Deoxyinosine-containing primers vs degenerate primers for polymerase chain reaction based on ambiguous sequence information, Molecular and Cellular Probes, 8(2):91-98 (1994).
Santin, M. et al., In vitro evaluation of the inflammatory potential of the silk fibroin, Journal of Biomedical Material Research, 46(3):382-389 (1999).
Sayre, R.M. et al, Physical Sunscreens, Journal of the Society of Cosmetics Chemists, 41(2):103-109 (1990).
Sofia, S. et al., Functionalized silk-based biomaterials for bone formation, Journal of Biomedical Materials Research, 54(1):139-148 (2001).
Thiele, J. J. et al., Vitamin E: Critical Review of Its Current Use in Cosmetic and Clinical Dermatology, Dermatologic Surgery, 31(7):805-813 (2005).
Vagenende, V. et al., Mechanisms of protein stabilization and prevention of protein aggregation by glycerol, Biochemistry, 48(46):11084-11096 (2009).
Written Opinion for PCT/US2013/037613, 8 pages (dated Jul. 29, 2013).
Yucel, T. et al., Non-equilibrium silk fibroin adhesives, Journal of Structural Biology, 170(2):406-412 (2010).
Zapata, G. et al., Engineering linear $F(ab')_2$ fragments for efficient production in *Escherichia coli* and enhanced antiproliferative activity, Protein Engineering, 8(10):1057-1062 (1995).
Lu, Shenzhou, et al. "Insoluble and Flexible Silk Films Containing Glycerol." Biomacromolecules 11.1 (2010): 143-150.
Brown, J. et al., Thermal and Structural Properties of Silk Biomaterials Plasticized by Glycerol, Biomacromolecules, 17:3911-3921 (2016).

\* cited by examiner

MODIFIED SILK FILMS CONTAINING GLYCEROL

CROSS REFERENCE TO RELATED APPLICATIONS

This application is a continuation of U.S. application Ser. No. 13/122,837, filed May 31, 2011, which is a 35 U.S.C. § 371 National Phase Entry Application of International Application No. PCT/US2009/060132, filed Oct. 9, 2009, which designates the U.S., and which claims benefit under 35 U.S.C. § 119(e) of U.S. Provisional Application No. 61/104,135 filed Oct. 9, 2008, the contents of which are incorporated herein by reference in their entirety.

GOVERNMENT SUPPORT

This invention was made with government support under grant EB002520 awarded by the National Institutes of Health and grant FA9550-07-1-0079 awarded by the United States Air Force. The government has certain rights in the invention.

FIELD OF THE INVENTION

The present invention provides for compositions and methods for preparing silk fibroin films containing glycerol and having improved mechanical properties.

BACKGROUND

Silk fibroin has excellent film-forming capabilities and is also compatible for use in the human body. Silk fibroin films, without further manipulation or treatment, are soluble in water because of dominating random coil protein structures. The structural features of the protein can be transformed from random coil to β-sheet structure by several treatments, including mechanical stretching, immersion in polar organic solvents, or curing in water vapor. This structural transition results in aqueous insolubility, thus providing options for the use of the material in a range of biomedical and other applications. Some pure silk fibroin films tend, over time, to become stiff and brittle in the dry state, however, exhibiting impressive tensile strength but low ductility. There remains a need to modify the physical and mechanical properties of silk fibroin films to improve mechanical properties and provide for more flexible silk fibroin-based systems for biomedical and other applications.

SUMMARY OF THE INVENTION

The present invention provides for films comprising silk fibroin and glycerol, which have distinct properties compared with silk fibroin films lacking glycerol. More specifically, the aqueous solubility and biocompatibility are enhanced with the use or inclusion and use of glycerol as a plasticizer. Processing silk fibroin in water also enhances both biocompatibility and the potential to load bioactive compounds without loss of function, and adds "green chemistry" value to these biomaterials. For example, blends of silk fibroin and glycerol with glycerol concentrations above 30% (w/w) cast into films resulted in the conversion of silk secondary structure from random coil to α-helix, prevented silk from dissolution upon hydration, provided distinct film nanostructure morphology, improved film flexibility in either dry (as-cast film) or wet (after leaching out the glycerol) environments, and preserved cell biocompatibility. Mechanistically, glycerol may replace water in silk fibroin chain hydration, resulting in initial stabilization of helical structures as opposed to random coil or β-sheet structures. The impact of glycerol on stabilizing film structure, aqueous insolubility and function apparently occurs above a glycerol concentration of about 20 wt % glycerol. The use of glycerol in combination with silk fibroin in materials processing expands the functional features attainable with this fibrous protein, and the formation of more flexible films with potential utility in biomaterial and device applications.

The present invention provides for a silk film comprising silk fibroin and from about 10% (w/w) to about 50% (w/w) glycerol, in which the film is prepared by entirely aqueous processes, and the silk film is ductile and substantially aqueous-insoluble. Many embodiments of the silk/glycerol blend films of the present invention exhibit higher ductility than silk films lacking glycerol, optionally following methanol treatment or water-annealing. The glycerol in the silk fibroin film, without being bound by theory, appears to stabilize the α-helical structure of the silk fibroin. Thus, in one embodiment, the ductile silk fibroin film may be converted from α-helical structure to β-sheet structure by extracting glycerol from the silk film and re-drying the film.

In one embodiment, a composition comprising glycerol modified silk film may be used as a 2-dimensional or 3-dimensional construct for tissue engineering, and may further comprise at least one active agent. Such tissue engineered construct may be used for organ repair, organ replacement, or other regenerated tissue materials such as cardiac muscle or cornea tissues. A 3-dimensional tissue engineering embodiment may be made by wrapping or shaping a ductile silk/glycerol film around a device or implant, such as a dental implant, and allowing the film to dry. Silk/glycerol blends may be formed, or the films folded or shaped, into sponges or blocks or other 3-dimensional structures. Optionally, the glycerol may then be leached out from the silk. Thus, the silk film may also be used as coatings on biomedical materials such as medical devices, tissue-engineered materials or implants, by coating the surfaces of such structures with a silk/glycerol ductile film. Coating from such modified silk film provides for improved compatibility and conforms well to the contours of the substrate.

In another embodiment, the glycerol-containing silk fibroin film is a composite material comprising a silk-based structure, such as silk fibroin nanospheres or microspheres, optionally containing active agents. Additionally, the silk composite material may include a silk-based composite support surface, such as a 3-dimensional structure of a medical implant or device, on which the ductile glycerol/silk film is shaped.

The embodiments of the prevent invention also provide for methods of preparing a silk film which is substantially aqueous-insoluble, by blending a silk fibroin solution with glycerol, wherein the concentration of glycerol in the silk fibroin/glycerol blend solution ranges from about 10% to 50% (w/w); casting the silk fibroin/glycerol blend solution onto a film-supporting surface; and drying the film. Silk films prepared by this process exhibit increased ductility compared with silk films lacking glycerol.

At least one active agent may be embedded in the ductile silk film by blending a silk fibroin solution with at least one active agent and glycerol before casting and drying the film. Similarly, cells or tissues may be embedded in the silk/glycerol blend films.

BRIEF DESCRIPTION OF THE DRAWINGS

FIG. 2A: blend films directly after film casting. FIG. 2B: blend films after 90% (v/v) methanol treatment for 1 hour. FIG. 2C, 20% (w/w) glycerol film with and without water treatment for 1 hour. *significant differences between groups ($P<0.01$). Data represent the ave±SD (n=4).

FIG. 3A, tensile strength. FIG. 3B, elongation at break. FIG. 3C, tensile modulus of dry blend films. FIG. 3D, tensile modulus of wet blend films after water treatment for 1 hour. *significant differences between groups ($P<0.01$). Data represent the average±SD (n=5).

FIG. 4A, glycerol content 10% (w/w). FIG. 4B, glycerol content 20% (w/w). FIG. 4C, glycerol content 30% (w/w), water treated for 1 hour. FIG. 4D, glycerol content 0%, methanol treated for 1 hour. Scale bar=200 nm.

FIGS. 5A and 5D show different regions in the film. FIG. 5B, high magnification of 5A. FIG. 5C, side view of 5A.

FIG. 6A shows microscopic images of cultured fibroblasts on 30% (w/w) glycerol/silk film, pure silk film, and tissue culture plastic (TCP). FIG. 6B depicts attachment of fibroblasts on different films.

DETAILED DESCRIPTION

Figure 1:
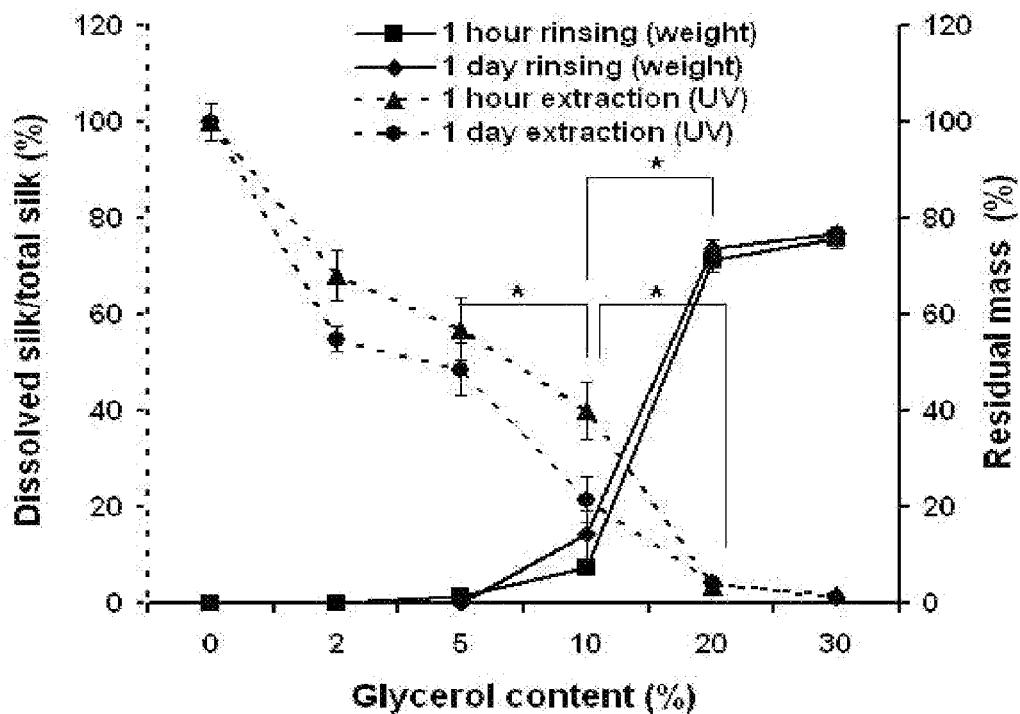
FIG. 1 shows data on the dissolution of silk and glycerol from blend films. *Significant differences between groups ($P<0.01$). Data represent the ave±SD (n=4).

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

Silk fibroin has excellent film-forming capabilities and is also compatible for use in the human body. Altman et al., 24 Biomats. 401-16 (2003); Vepari & Kaplan, 32 Prog. Polym. Sci. 991-007 (2007). Silk fibroin films have good dissolved oxygen permeability in the wet state, similar to that of human skin, which suggests potential applications for these films in wound dressing and artificial skin systems. Minoura et al., 11 Biomats., 430-34 (1990); Minoura et al., 31 Polymer, 265-69 (1990a). Films formed from silk fibroin, without further manipulation, are soluble in water, however, because of dominating random coil protein structures. The structural features of the protein can be transformed from random coil to β-sheet form by treatment with heating (Hu et al., 41 Macromolecules 3939-48 (2008)), mechanical stretching (Jin & Kaplan, 424 Nature 1057-61 (2003)), immersion in polar organic solvents (Canetti et al., 28 Biopolymers—Peptide Sci. § 1613-24 (1989)), and curing in water vapor (Jin et al., 15 Adv. Funct. Mat. 1241-47 (2005)). This structural transition results in aqueous insolubility, thus providing options for the use of the material in a range of biomedical and other applications such as sensor platforms. Zhang, 16 Biotechnol. Adv. 961-71 (1998). Some pure silk fibroin films tend, over time, to become stiff and brittle in the dry state, however, exhibiting impressive tensile strength but low elongation. Jin et al., 2005. Therefore, there remains a need to modify the physical and mechanical properties of silk films to control properties, mainly towards more flexible systems.

Blending polymers with plasticizers is a traditional approach to address ductility and tensile strength as outlined above. For example, some studies have suggested that silk film properties can be modified by blending silk with other synthetic or natural polymers, such as alginate, polyallylamine, chitosan, cellulose, poly(caprolactone-co-D,L-lactide), S-carboxymethyl keratin, poly(vinyl alcohol) (PVA), poly (ethylene glycol), and poly(ethylene oxide). See Liang & Hirabayashi, 45 J. Appl. Polymer Sci. 1937-43 (1992); Arai et al., 84 J. Appl. Polymer Sci. 1963-70 (2002); Kitagawa & Yabuki, 80 J. Appl. Polymer Sci. 928-34 (2001); Noishiki et al., 86 J. Appl. Polymer Sci. 3425-29 (2002); Kesenci et al., 12 J. Biomats. Sci. Polymer Ed. 337-51 (2001); Lee et al., 9 J. Biomats. Sci. Polymer Ed. 905-14 (1998); Tsukada et al., 32 J. Polymer Sci. B, 243-48 (1994); Gotoh et al., 38 Polymer 487-90 (1997); Jin et al., 5 Biomacromols. 711-17 (2004). For example, blends of silk fibroin and PEO show materials stabilization (Tin et al., 2004; Jin et al., 3 Biomacromol. 1233-39 (2002)), and the use of water as a plasticizer may improve film properties (Jin et al., 2005).

In many cases, however, improving blends to effect mechanical properties remains a challenge. In particular, avoiding additions of other polymers while generating systems that maintain stability for extended time frames remains a goal. Thus, the present invention provides for alternative plasticizer options: in particular glycerol. Previously, silk fibroin films were immersed in 10% glycerin (10 minutes at 95° C.), and conditioned in a humidity rich drier to effect crystal transformation from of silk I to II. Kawahara et al., 291 Macromol. Mater. Eng. 458-62 (2006). Also, the addition of 3%-8% glycerin reduced phase separation of silk fibroin/PVA blends. Dai et al., 86 J. Appl. Polymer Sci. 2342-47 (2002). In both of these approaches, silk fibroin solution was generated by dissolving degummed silk in the ternary solvent system of $CaCl_2/CH_3CH_2OH/H_2O$.

In the methods of the present invention, glycerol was blended with an aqueous-dissolved silk fibroin solution and then cast into films. These films were assessed for mechanical properties and structural features to better understand the interactions between the silk fibroin and glycerol. Specific interactions between silk fibroin and glycerol provide benefits to the film properties, perhaps enacted by affecting silk fibroin crystallization behavior in the formation of the β-sheets as the stabilizing physical cross-links in the films, without the necessary addition of other polymers.

The present invention also provides for silk films with distinct aqueous dissolution properties, and methods for adjusting the dissolution properties of silk films by blending silk fibroin solution with the suitable amount of glycerol. In particular, the dissolution in water of silk fibroin from silk/glycerol blend films was measured by UV absorbance, because silk fibroin has significant tyrosine content (>5 mole %) that, unlike glycerol, absorbs at 280 nm wavelength. After a rapid initial weight loss in the first hour, no further significant difference was found for the residual mass and dissolved silk content over time (FIG. 1). When the glycerol content in the silk/glycerol blend films was 2% and 5% (w/w), the films completely dissolved in water, similar to the control silk films that contained no glycerol (FIG. 1). Therefore, glycerol at concentrations lower than about 5% (w/w) did not appear to have significantly changed silk film properties.

When the glycerol content in the films was increased from about 10% to 20% (w/w), the residual mass of the films that remained insoluble increased from about 10% to about 75%, respectively ($p<0.01$, FIG. 1). Further increases in glycerol to about 30% (w/w) reduced solubility further, although the results were not statistically significant when compared to the 20% glycerol data. These results indicated that 20% (w/w) glycerol is a concentration that induces significant changes in silk film properties, resulting in substantial insolubility of the material in water (i.e., about 75% residual mass retained after soaking in aqueous solution). When the glycerol content was significantly below 20% (w/w), the amount of silk that dissolved in water decreased as the glycerol content increased. At 20% (w/w) glycerol, less than 5% of the total silk mass was soluble in water, much lower than that from 10% (w/w) glycerol films ($p<0.01$, FIG. 1). From the residual mass determinations, the 20% (w/w) glycerol film lost approximately 25% of the total mass in water. Thus, in comparing masses, initial glycerol contents and UV absorbance of the solubilized material, blend films containing more than about 30% (w/w) glycerol lost almost all the glycerol in water while the silk fibroin protein remained stable in the films, likely due to glycerol-induced change in silk structure. This result was not observed at the lower glycerol contents.

Figure 2A:
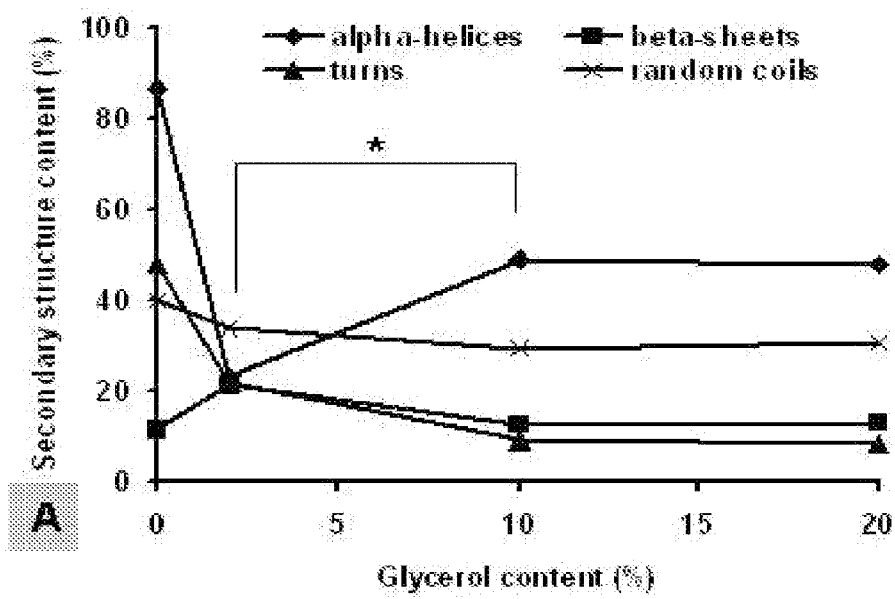
FIGS. 2A-2C show FTIR determination of silk secondary structures in blend films with different glycerol content.

Changes in film solubility due to glycerol content indicate that glycerol induces structural changes in the silk fibroin. The self-assembly process of silk fibroin protein into water-insoluble fibers is accompanied by increased β-sheet structure content, or silk II, or crystalline structures. Kaplan et al., in PROTEIN BASED MATS., 103-31 (McGrath, ed., Birkhauser, Boston, Mass., 1998); Motta et al., 203 Macromol. Chem. Phys. 1658-65 (2002); Chen et al., 89 Biophys. Chem. 25-34 (2001). In vitro, the silk II structure can be obtained by solvent treatment, such as with methanol and ethanol. Cast silk films after water annealing (exposure of cast films in water vapor for 24 hours), exhibit stable silk I structure with increased type II β-turns. Jin et al., 2005. Once formed, the silk I structure in water-annealed films does not transition to the silk II structure, even with methanol treatment. In the silk fibroin/glycerol films of the present invention, the α-helical structure content is apparently increased up to approximately 50%, while the β-turn content decreased in the blend films having a glycerol content higher than 10% (w/w) ($p<0.01$, FIG. 2A). These structural changes were distinguished from the changes observed in methanol-treated and water-annealed silk films prepared in the absence of glycerol.

Figure 2B:
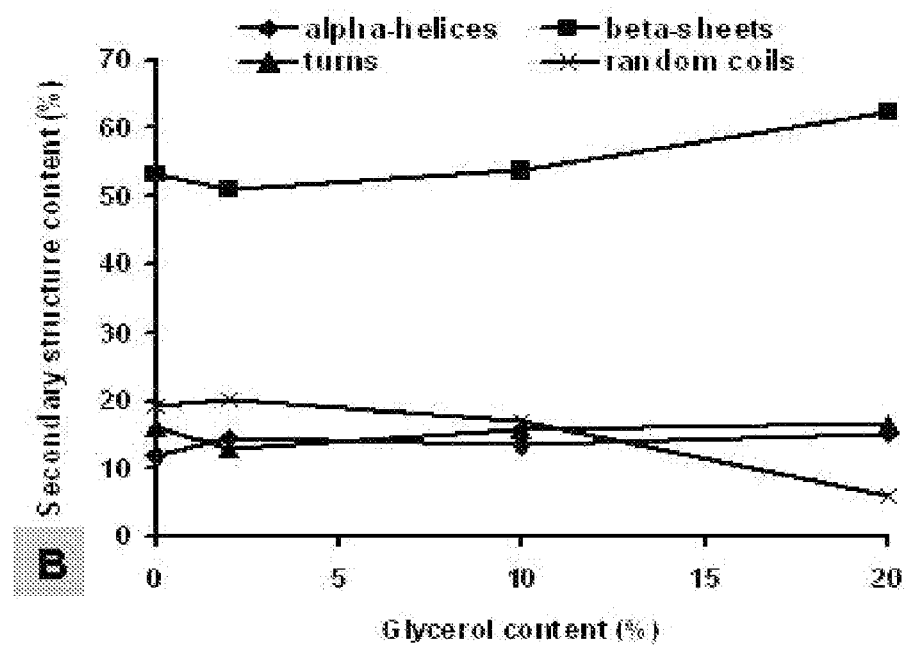

The secondary structure content remained relatively unchanged when the glycerol content in the films was increased from about 10% to 20% (w/w). Thus, stable α-helical structures apparently dominate the glycerol blended material. A three-fold helical crystal structure (silk III) has been reported previously for silk at air-water interfaces using the Langmuir-Blodgett technique, reflecting the amphilicity features of silk (Valluzzi et al., 24 Int'l J. Biol. Macromol. 237-42 (1999)), but not in glycerol modified silk materials. The silk III structure can be transformed into the more stable silk II if the compression force was more than 35 $mNm^{-1}$. The amino acid side chain distributions along the helix and the orientation of the chain axis have been well-characterized in these studies. Valluzzi et al., 1999. For the glycerol/fibroin blend silk films, after methanol treatment, β-sheet structure content increased to about 50%-60%, while α-helical structure content decreased to about 20%, regardless of the glycerol content in the films (FIG. 2B). This response, in terms of structural transitions induced by methanol, is different from that observed with the water-annealed silk films where no conformational transition from α-helical to β-sheet occurs upon methanol treatment. Jin et al., 2005. Furthermore, after the 20% (w/w) glycerol blended silk films were rinsed with water and re-dried in the air, α-helical structure content decreased while β-sheet and β-turn structure content increased to approximately 45% and 20%, respectively ($p<0.01$, FIG. 2C). Therefore, for glycerol blend silk films, stable silk II structures (crystalline, β-sheets) can be obtained by leaching out the glycerol and re-drying the film.

Mechanistically, glycerol appears to alter the silk fibroin intramolecular and intermolecular interactions and result in a conformational transition from random coil to α-helices, typically regarded as an unstable intermediate state toward stable β-sheet structure formation. The presence of glycerol appears to stabilize the α-helical structure, however, preventing further transition toward β-sheet structures. It appears that the concentration of glycerol may reach a critical level to achieve this extent of structural control. For 20% and 50% (w/w) glycerol/fibroin blend films, the molar ratios between glycerol and silk fibroin are approximately 1000:1 and 4000:1, respectively. After immersion in an aqueous solution where the glycerol leaches out, the blend film may still contain some α-helical structure, most likely due to the stabilizing effect of residual bound glycerol molecules. This could be the reason that the wet films (immersed in water) remained flexible when compared to non-glycerol containing films after methanol treatment. The silk structural transition from α-helix to β-sheet may occur during the film re-drying process, due to increased silk concentration and intermolecular interactions between silk fibroin molecules. As a result, the re-dried films become somewhat brittle, similar to methanol-treated silk fibroin films.

As defined herein, 'dry blend films' refers to silk films prepared by directly casting the silk fibroin/glycerol blend solutions to form films and then drying the films overnight. 'Wet blend films' refers to the same cast and dried films that are subsequently immersed and extracted in ultrapure water at 37° C. for 1 hour, which dissolves out glycerol, and dried again in the air. Accordingly, the dry environment refers to the environment leading to the 'as-cast' silk fibroin/glycerol blend film, and the wet environment refers to the steps comprising a further treatment of the 'as-cast' silk fibroin/glycerol blend film to withdraw glycerol from the film.

Figure 3A:
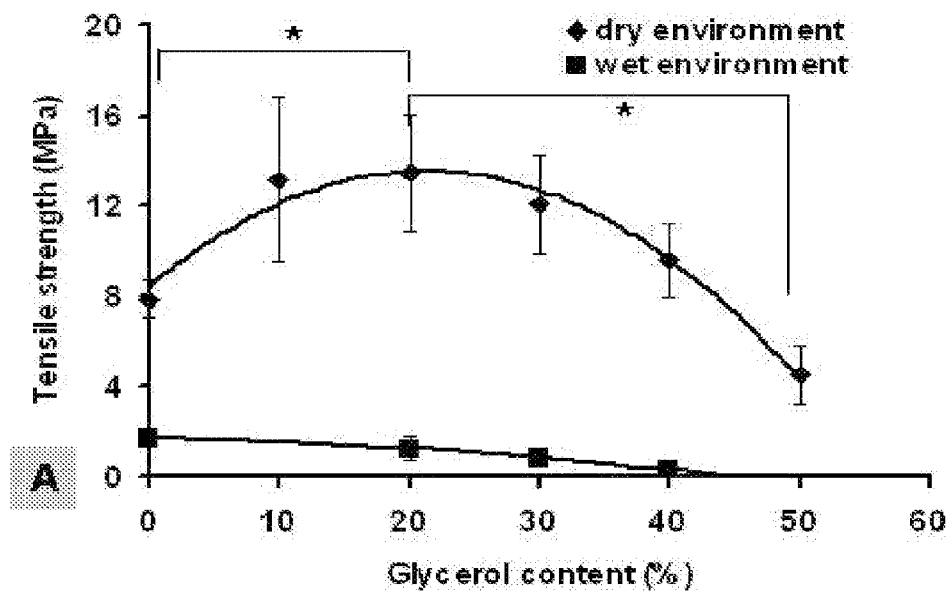
FIGS. 3A-3D present mechanical properties of blend films with different glycerol content.
Figure 3B:
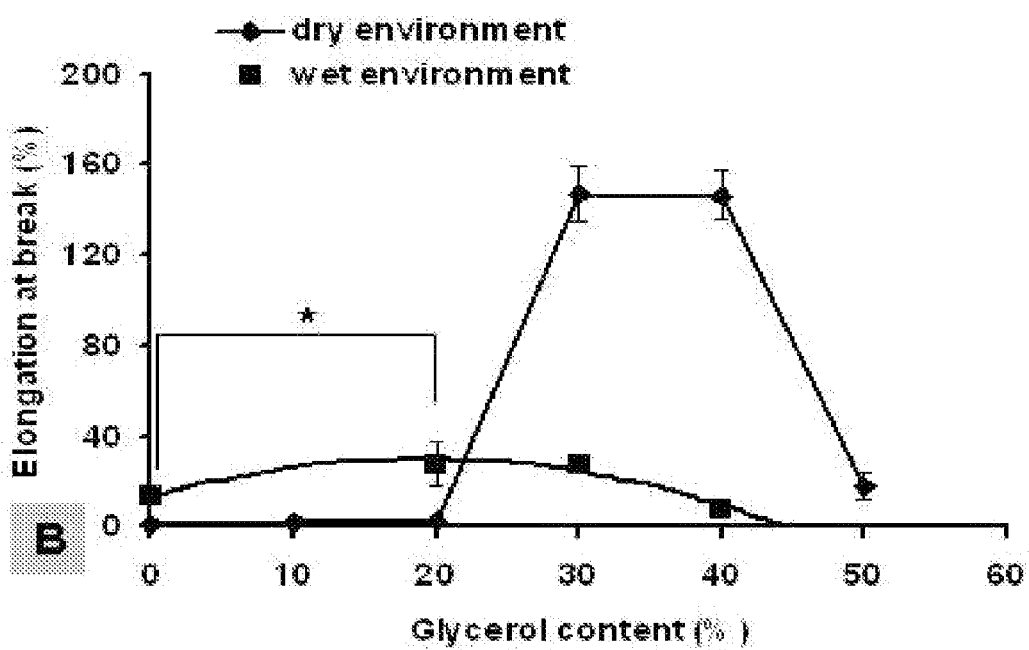

The mechanical properties of the silk fibroin/glycerin films of the present invention were also examined. The tensile strength of dry blend films changed with a change in glycerol content in the films. When the glycerol content increased from 0% to about 20% (w/w), the tensile strength significantly increased from about 8 MPa to 13 MPa ($p<0.01$, FIG. 3A). When the glycerol content was increased above 20%, tensile strength significantly decreased. At 40% glycerol, the tensile strength was about 4 MPa, significantly lower than that of the 0% and 20% (w/w) glycerol films ($p<0.01$, FIG. 3A). The tensile strength of glycerol-depleted films (films after glycerol has leached out) did not change significantly with change in glycerol content, with less than 2 MPa determined for all samples ($p>0.05$, FIG. 3A). For the dry blend films, elongation at break remained low (below 3%) when the glycerol content was below 20% (w/w). These values significantly increased to approximately 150% when the glycerol content was increased to 30% and 40% (w/w). At 50% (w/w) glycerol, the elongation at break values decreased to less than 20%. The trend was similar for that of tensile strength except that the highest elongation at break was obtained at 30%-40% (w/w) glycerol rather than 20% (w/w) glycerol with highest tensile strength. For the wet blend films, the elongation at break of the 20% (w/w) glycerol films was about 27%, significantly higher than that of the 0% and 40% glycerol films (14% and 8%, respectively) ($p<0.01$, FIG. 3B). Therefore, compared to methanol-treated silk films without glycerol, the glycerol blend films had higher ductility in both the dry and wet states, a useful property for many applications.

Figure 3C:
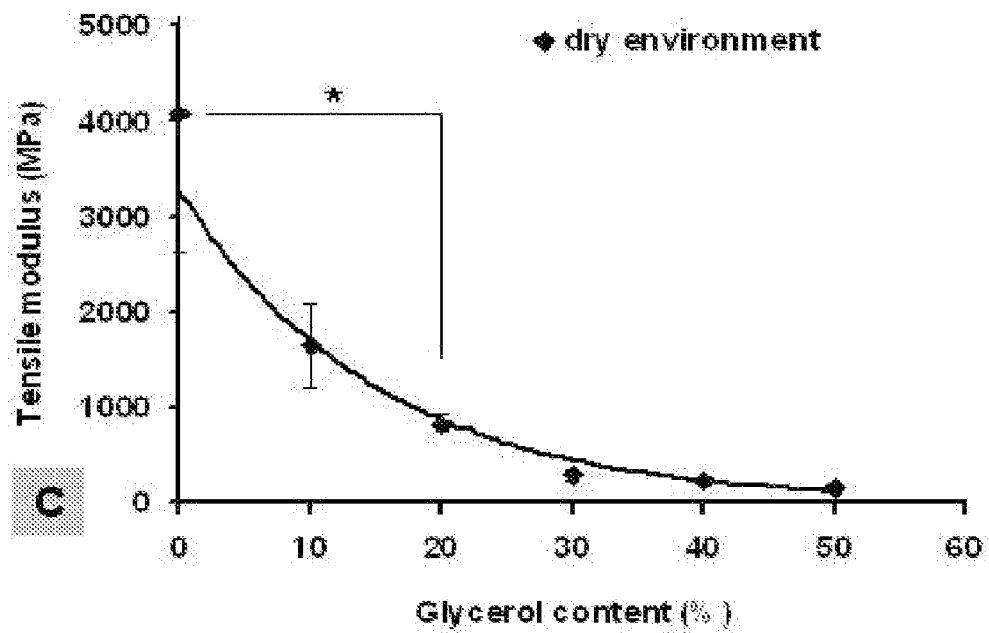
Figure 3D:
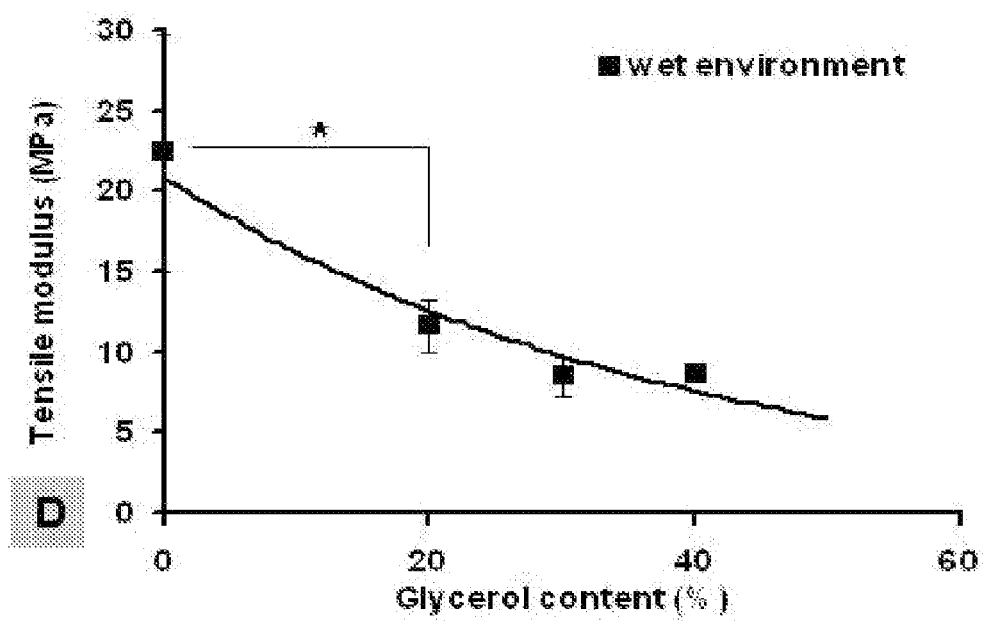

The ductility of the glycerol-silk films was also greater than that of water-annealed silk films, as water-annealed films exhibited elongation at break of about 6% (Jin et al., 2005), which is 25-times lower than that of the 30% glycerol silk films presented herein. Free-water content may also influence the flexibility of silk films. Kawahara et al., 2006. Blends with glycerol may preserve the free-water content in the silk films and, therefore, improved film flexibility. The role of glycerol in helical content of the silk fibroin may also play a role in the mechanical behavior of the films. When the glycerol content was increased from 0% to 40% (w/w), the tensile modulus decreased about 17-fold in the dry blend films, and about 2.5-fold for the wet blend films (FIGS. 3C and 3D). Apparently, with more glycerol in the blends the films became mechanically weaker, and this effect was more pronounced for the dry blend films. The tensile modulus of dry silk fibroin/glycerol blend films was more than 100-times higher than the corresponding wet blend, glycerol-depleted films from which glycerol had been leached-out.

Figure 2C:
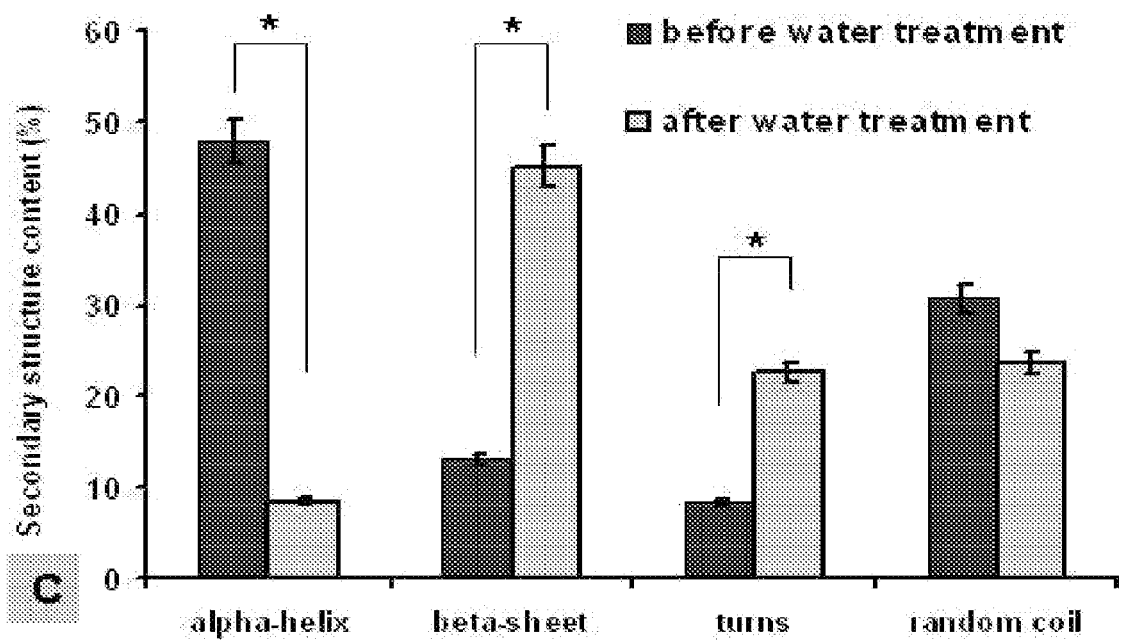
Figure 4:
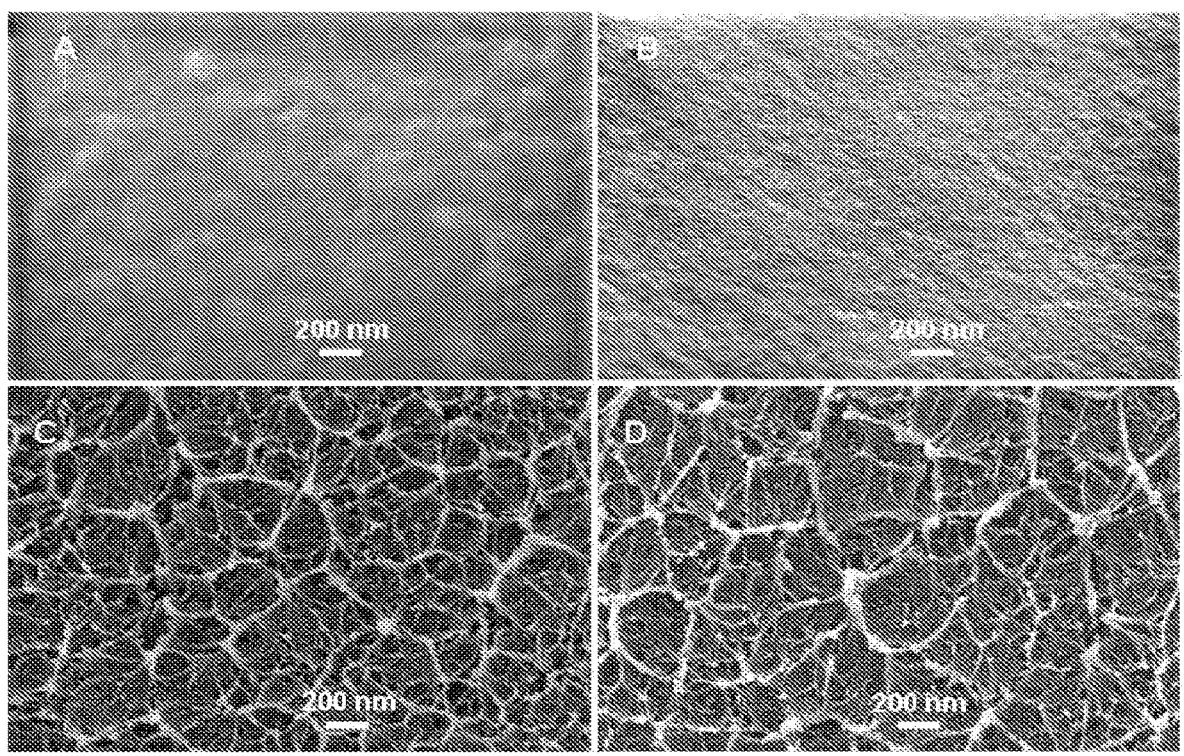
FIGS. 4A-4D show SEM images of blend films.

The nano-structures of silk fibroin in the silk blend films were analyzed by morphological characterization to further assess the impact of glycerol on film properties. Silk films were fractured in liquid nitrogen and the cross sections of the films examined by SEM. Silk fibroin protein formed globular nano-structures with diameters of 100 nm-200 nm when the glycerol content was 10% (w/w) (FIG. 4A). The globules, however, were not observed when 20% (w/w) glycerol was blended in the film: the blend films had relatively smooth morphologies when viewed by SEM (FIG. 4B). These results indicate that a high content of glycerol (>20% w/w) influences silk fibroin self-assembly and nano-structure features. Interestingly, when the 20% (w/w) glycerol silk films were treated with water to leach out the glycerol and then re-dried in the air, the silk fibroin self-assembled into nano-filaments, similar to those observed in methanol-treated pure silk films (FIGS. 4C and 4D). This observation is consistent with the secondary structure transitions with β-sheet structure formation in both water-treated and methanol-treated glycerol silk films (FIGS. 2B and 2C). Therefore, the formation of nano-structures in glycerol-blended films correlated with the structural features in the films, and was likely influenced by silk secondary structural changes.

Figure 5:
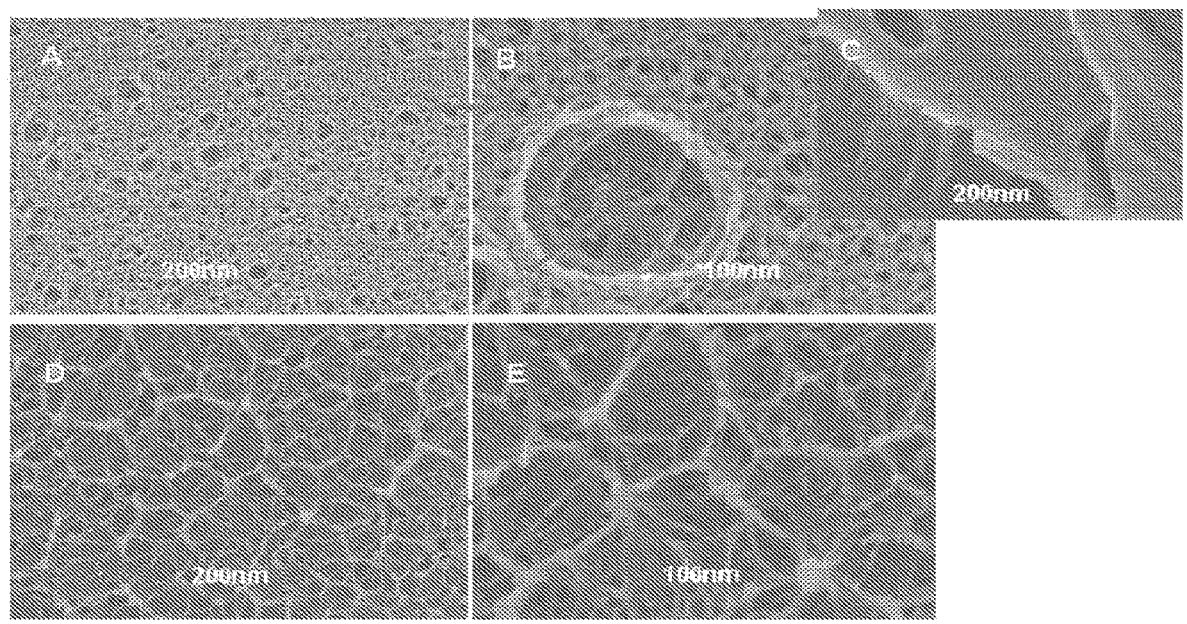
FIGS. 5A-5D are micrographs showing nano-filament structures in water-treated silk films containing 30% (w/w) glycerol.
FIG. 5E, high magnification of 5D. Scale bar=200 nm in 5A, 5C, 5D; 100 nm in 5B, 5E.

The silk nano-filament structures that had formed in the 30% (w/w) glycerol films after water treatment were further studied by SEM (FIGS. 5A, 5D). The nano-filament structures were more clearly visible at higher magnification (FIGS. 5B and 5E) and in side view (FIG. 5C). In different regions of the film, distinguished morphologies and organization of nano-filaments was observed (compare FIGS. 5A, 5B and 5D, 5E), probably due to inhomogeneous drying rates during silk film casting. The size of the nano-filaments, however, was consistently about 10 nm-20 nm throughout the film.

Figure 7:
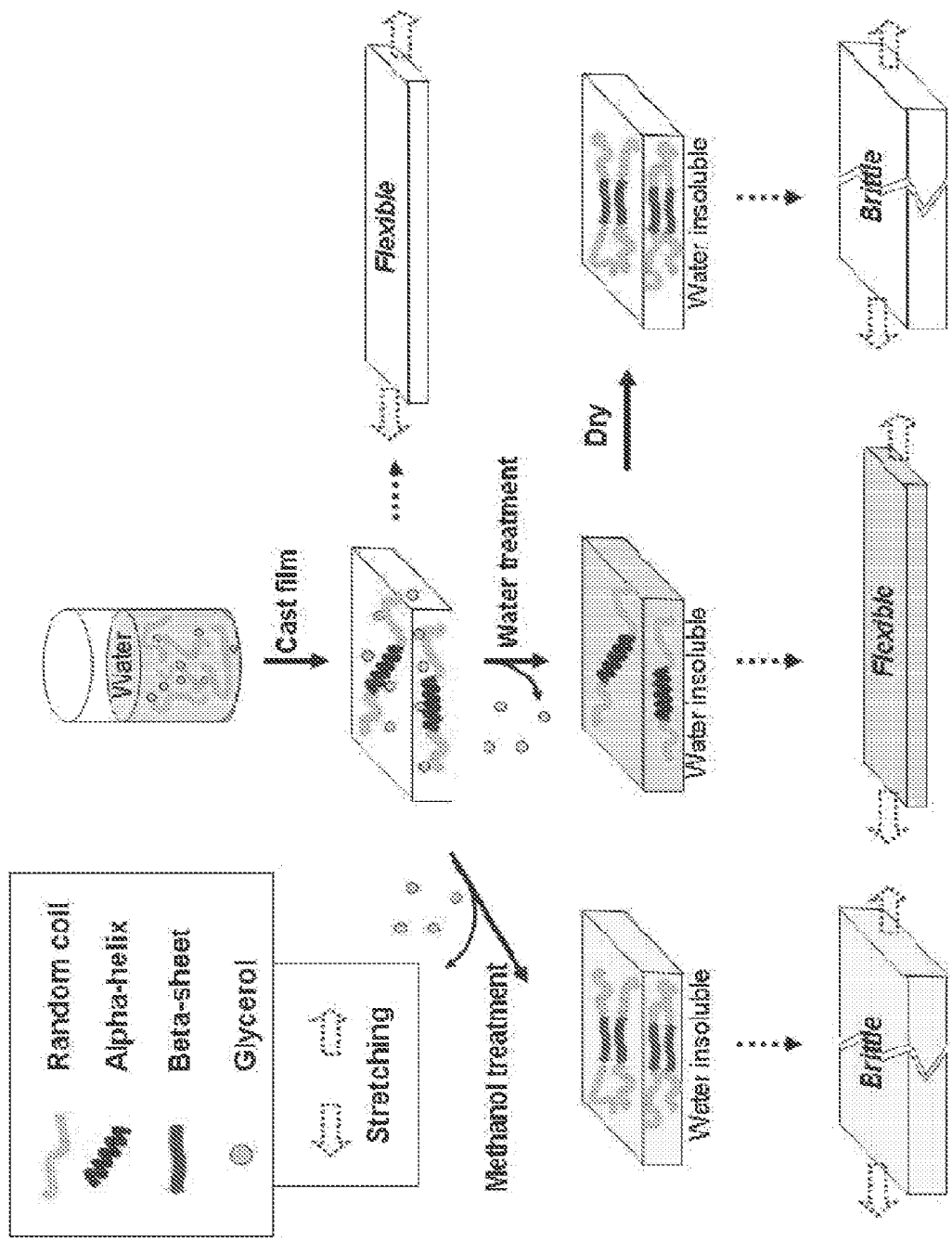
FIG. 7 is a schematic illustration of silk structural transitions in glycerol-blended silk films.

The glycerol content in silk films may be important for controlling silk secondary structural transitions and influencing the mechanical properties of the films. Glycerol molecules may interact with silk fibroin chains via intermolecular forces, most likely hydrogen bonds between hydroxyl groups of glycerol and amide groups of silk. Dai et al., 86 J. Appl. Polymer Sci. 2342-47 (2002). This interaction may alter the hydrophobic hydration state of protein chains, as these are hydrophobic proteins due to the high content of glycine-alanine repeats (Bini et al., 335 J. Mol. Biol. 27-40 (2004)), and therefore induce silk secondary structural change from predominant random coils (silk solution state or as cast film) to α-helices (FIG. 7). This interaction may stabilize the helical stage of silk unless the film has been treated by solvents, such as water and methanol. Upon solvent treatment, some glycerol molecules solubilize from the films and diffuse into the surrounding medium, although tightly bound glycerol molecules likely stay associated with the silk fibroin chains, stabilizing silk α-helical structures and preserving film flexibility. Water molecules that replace leached-out glycerol and form weaker hydrogen bonds with fibroin molecules might also contribute to maintaining silk structure and mechanical properties. When these glycerol-depleted films are re-dried, the strong intermolecular interactions between silk molecules may dominate, promoting a structural transition from α-helices to the more thermodynamically stable β-sheets (FIG. 7). Such process is similar to the previously reported mechanism of silk structural transitions based on the change in hydrophobic hydration state of the protein chains. Matsumoto et al., 110 J. Phys. Chem. B 21630-38 (2006).

Although some of the interactions of glycerol in silk film mechanics have been explored (Kawahara et al., 291 Macromol. Mater. Eng. 458-62 (2006); Dai et al., 86 J. Appl. Polymer Sci. 2342-47 (2002)), the particular formulation and, importantly, the function of the glycerol in the present invention is distinct from those reported previously. For instance, the tensile properties of silk/PVA blend films were modified by inclusion of up to 8% glycerol in the silk/PVA blend. The tensile strength and elongation at break for the silk/PVA films were about 350 kg/cm$^3$ and 10%, respectively. When 5% glycerol was blended with PVA/silk film to reduce phase separation, the resulting film tensile strength and elongation at break were 426 kg/cm$^2$ and 53%, respectively. Increasing the concentration of glycerol to >5%, however, significantly reduced the tensile strength of silk/PVA blend films. Dai et al., 2002. By contrast, in one embodiment of the present invention, incorporating 30% glycerol in the fibroin silk film significantly improved both the tensile strength (to about 12 MPa) and elongation at break (150%), without the incorporation of PVA.

In another study, glycerol solution was used as a post-treatment of pure silk film to convert the silk structure from silk I to silk II (β-sheet structure). More specifically, silk film was immersed in 10% glycerol solution, heated at 95° C., and dried at 50% relative humidity. Although the glycerol-soaked film underwent self-expansion after the soaking treatment, its ductility was not assessed. Kawahara et al., 2006. In contrast, in some embodiments of the present invention, silk fibroin solution is blended with glycerol and cast into highly ductile films, as demonstrated by the improved tensile strength and elongation at break of the silk films containing about 10% to 50% glycerol.

The glycerol blended silk films presented herein demonstrate unique features of diverse and controllable silk structure transitions, desired mechanical properties, and ease of fabrication (one-step film casting without further treatments). These features suggest that these films have utility in biomedical applications.

The present invention thus provides for methods of preparing silk films with increased tensile strength and ductility. The methods comprise blending a silk fibroin solution with glycerol, where the concentration of glycerol in the silk fibroin/glycerol blend solution is about 10% to 50% (w/w); casting the silk fibroin/glycerol blend solution onto a film-supporting surface; and drying the film. This simple process confers the silk films of present invention with designable tensile strength and ductility, depending on the concentration of glycerol, offering an alternative to silk films prepared silk fibroin solution in absence of glycerol. In addition, silk blend films comprising other biopolymers, such as PVA and PEO, may also be modified by glycerol to enhance the flexibility or ductility of the silk/biopolymer blend film, employing the same process as described above.

Additionally, the glycerol silk blends of the present invention may be combined with other silk-based structures to form 3-dimensional silk scaffolds, silk sponges, or other silk composite structures having 3-dimensional structures, for applications such as drug delivery systems, tissue engineered materials or other biomedical devices. For example, the ductile silk film of the present invention may be combined with silk fibroin nanospheres or microspheres carrying an active agent to provide sustained release of the active agent. As another example, silk fiber-based composite comprising silk fibers optionally coated with silk fibroin solution or silk gel may be combined with the ductile silk film of the present invention to provide flexible fibrous materials for use as optical fiber or muscle fibers. Glycerol can be easily blended with any silk composite to alter the mechanical properties of the silk-based structure. Alternatively, silk-based composite may be wrapped or shaped with a ductile silk/glycerol film around the contour of the silk-based structure. All of the silk composites described herein can be easily functionalized with drugs, antibiotics, cell responses molecules, dyes, enzymes and other small and large molecules, with retention of function.

With improved flexibility of silk film or silk blend film by glycerol modification, the processes of the present invention may be used to modify a variety of silk blend films or coatings in a variety of medical applications such as wound closure systems, including vascular wound repair devices, hemostatic dressings, sponges, patches and glues, sutures, drug delivery (WO 2005/123114), biopolymer sensor (WO 2008/127402), and in tissue engineering applications, such as, for example, tissue-engineered organs or other biodegradable implantation into the human body (WO2004/0000915; WO2008/106485). The improved flexibility of silk film is advantageous as it may provide flexible expandability or contractibility to the biomedical material as required by some applications such as functional dressing materials or tissue materials such as muscle tissue. For example, a ductile silk film of the present invention may be shaped around a structure (such as an implant). The silk film may comprise additional active agents selected to further the purpose of the device, such as tissue or bone promoting agents in a dental device. Additionally, once the ductile film has been shaped to the structure, glycerol may be removed by leaching as described herein.

Figure 6A:
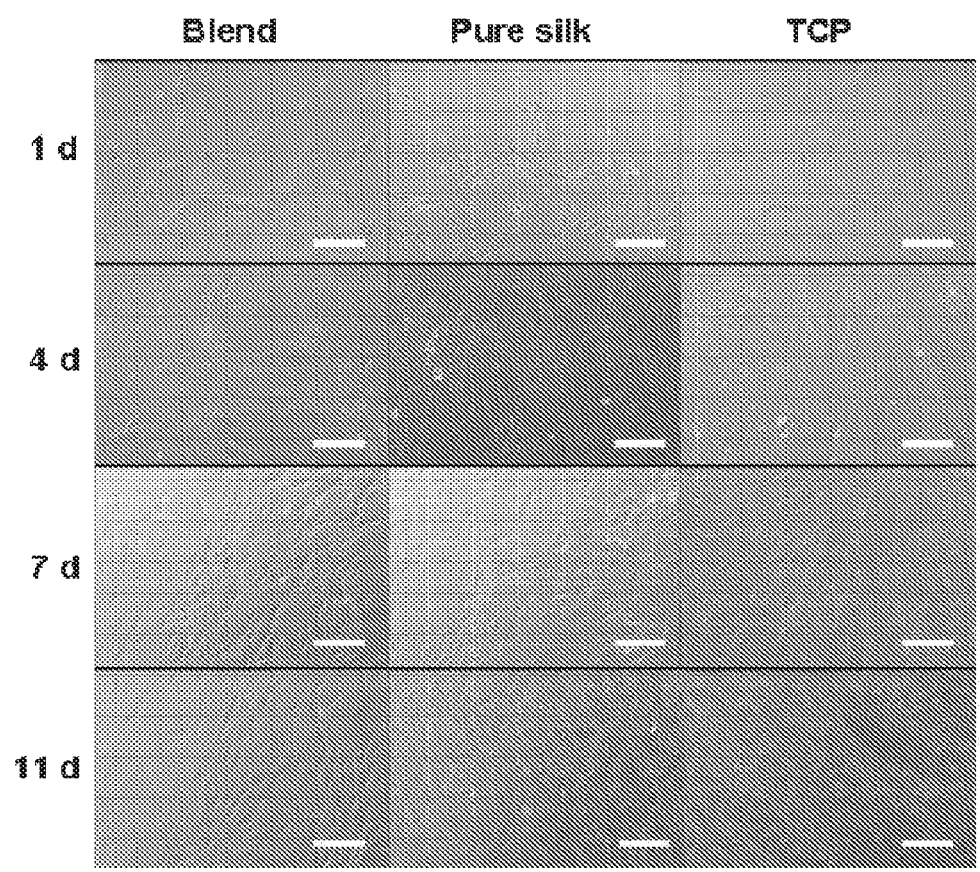
FIGS. 6A and 6B demonstrate attachment and proliferation of fibroblasts on different surfaces.
Figure 6B:
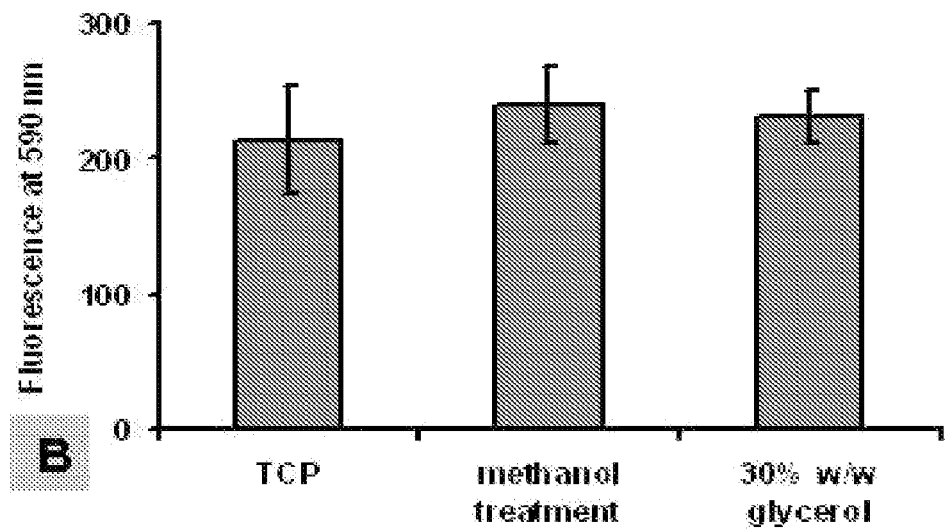
Figure 6C:
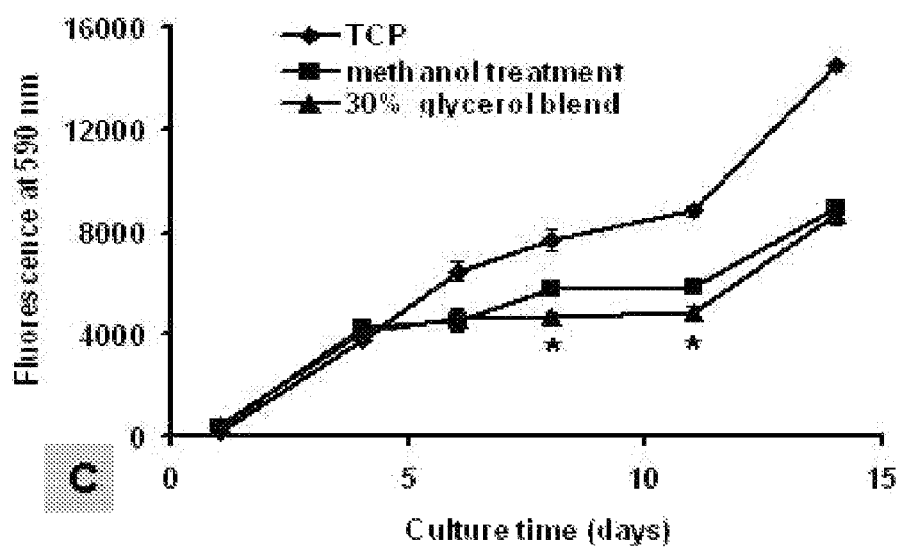
FIG. 6C shows proliferation of fibroblasts on different films. Data represent the average±SD (n=6). Bar=50 μm.

The silk fibroin/glycerol blend films of the present invention also provide a suitable platform for the attachment and proliferation of fibroblasts. Because of the modified and potentially useful mechanical properties for these silk blend films, the potential utility of such biomaterials in cell and tissue culture is important to assess. Thus, in preliminary studies, the attachment and proliferation of fibroblast cells on 30% (w/w) glycerol-silk films was compared with methanol-treated pure silk films and tissue culture plastic (TCP) as controls. Initial cell attachment (3 hours) on all three surfaces was similar (first row in FIG. 6A) and as quantified by Alamar Blue staining (FIG. 6B). Cell proliferation in fourteen days of culture, however, was different on the different surfaces. After four days culture, fibroblasts on TCP grew faster than those on pure silk films and blend silk films, an observation consistent with prior studies on pure silk films. (Sofia et al., 54 J. Biomed. Mater. Res. 139-48 (2001); Wang et al., 29 Biomats. 894-903 (2008). After fourteen days culture, the number of cells on TCP was about 1.8-times more than that on the silk films, and there was no significant difference between the pure silk films and blend silk films, as determined by Alamar Blue staining (FIG. 6C). The 30% (w/w) glycerol silk film only differed from the methanol-treated silk film for fibroblasts proliferation in the time period from six days to eleven days, in which cells grew faster on the methanol-treated film than on the glycerol film (p<0.01, FIG. 6C). RGD-modified silk films exhibit excellent surface properties to promote rapid attachment and proliferation of fibroblasts, osteoblast-like cells, and human bone marrow-derived mesenchymal stem cells. Chen et al., 67 J. Biomed. Mater. Res. A, 559-70 (2003). Thus, similar strategies could be employed with the silk-glycerol blend films.

The embodiments of the present invention thus provides for silk/glycerol film that may be suitable for a tissue engineered constructs that can be used for organ repair, organ replacement or regeneration strategies that may benefit from these modified silk materials. A tissue engineered construct comprising silk fibroin/glycerol blending material and optionally at least one bioactive agent such as a cell, may be used for organ repair, organ replacement or regeneration strategies including, but not limited to, spinal disc, cranial tissue, dura, nerve tissue, liver, pancreas, kidney, bladder, spleen, cardiac muscle, skeletal muscle, tendons, ligaments, cornea tissues, and breast tissues. Any type of cell can be added to the tissue-engineered construct for culturing and possible implantation, including cells of the muscular and skeletal systems, such as chondrocytes, fibroblasts, muscle cells and osteocytes, parenchymal cells such as hepatocytes, pancreatic cells (including Islet cells), cells of intestinal origin, and other cells such as nerve cells, bone marrow cells, skin cells, pluripotent cells and stem cells (including, e.g., embyonic stems, adult stem cells, and induced pluripotent stem cells), and combination thereof, either as obtained from donors, from established cell culture lines, or even before or after molecular genetic engineering. Pieces of tissue can also be used, which may provide a number of different cell types in a single structure.

Alternatively, the flexible silk/glycerol film may also be used as coatings on biomedical materials such as medical device, tissue-engineered materials or implants. As discussed above, the improved flexibility of the glycerol modified silk film may provide flexible expandability or contractibility to match the contractible properties of the biomedical material as required by some applications such as functional dressing materials or tissues such as muscle tissue. Because the modified silk film is less prone to break in elongation, contraction, stretch or deformation, coating from such film will provide for improved compatibility and will conform well to the contours of the substrate. The substrates or articles for coating of the modified silk film may include any number of tissues, regenerated tissue, medical device, medical implant, veterinary device, or veterinary implant. For example, a ductile silk/glycerol film may be wrapping around a device or implant, such as spine cages, coronary stents, dental implants or hip and knee prostheses.

As noted, silk/glycerol blend film may be modified to contain at least one active agent. The agent may be mixed with a silk fibroin solution prior to forming the silk blend film, or loaded into the silk blend film after it is formed. The variety of active agents that can be used in conjunction with the silk blend film of the present invention is vast. For example, the active agent may be a therapeutic agent or biological material, such as cells (including stem cells), proteins, peptides, nucleic acids (DNA, RNA, siRNA), nucleic acid analogues, nucleotides, oligonucleotides or sequences, peptide nucleic acids, aptamers, antibodies, hormones, hormone antagonists, growth factors or recombinant growth factors and fragments and variants thereof, cytokines, or enzymes, antibiotics, viruses, antivirals, toxins, prodrugs, chemotherapeutic agents, small molecules, drugs and combinations thereof. Exemplary active agent suitable for modifying the silk blend film of the present invention includes cells (including stem cells), erythropoietin (EPO), YTGSR peptides, glycosaminoglycans (GAGs), hyaluronic acid (HA), integrins, selectins and cadherins; analgesics and analgesic combinations; steroids; antibiotics; insulin; interferons α and γ; interleukins; adenosine; chemotherapeutic agents (e.g., anticancer agents); tumor necrosis factors α and β; antibodies; cell attachment mediators, such as RGD or integrins, or other naturally derived or genetically engineered proteins, polysaccharides, glycoproteins, cytotoxins, prodrugs, immunogens, or lipoproteins.

One or more active agents may be used to modify the silk/glycerol blend film. For instance, when using silk blend film of the present invention as a platform to support biological material such as cells, it may be desirable to add other materials to promote the growth of the agent, promote the functionality of the agent after it is released from the silk blend film, or increase the agent's ability to survive or retain its efficacy during the processing period. Exemplary materials known to promote cell growth include, but not limited to, cell growth media, such as Dulbecco's Modified Eagle Medium (DMEM), fetal bovine serum (FBS), non-essential amino acids and antibiotics, and growth and morphogenic factors such as fibroblast growth factor (e.g., FGF 1-9), transforming growth factors (TGFs), vascular endothelial growth factor (VEGF), epidermal growth factor (EGF), platelet derived growth factor (PDGF), insulin-like growth factor (IGF-I and IGF-II), bone morphogenetic growth factors (e.g., BMPs 1-7), bone morphogenetic-like proteins (e.g., GFD-5, GFD-7, and GFD-8), transforming growth factors (e.g., TGF-α, TGF-β nerve growth factors, and related proteins. Growth factors are known in the art, see, e.g., Rosen & Thies, CELLULAR & MOL. BASIS BONE FORMATION & REPAIR (R. G. Landes Co.). Additional material to be embedded in silk/glycerol film may include DNA, siRNA, antisense, plasmids, liposomes and related systems for delivery of genetic materials; peptides and proteins to active cellular signaling cascades; peptides and proteins to promote mineralization or related events from cells; adhesion peptides and proteins to improve film-tissue interfaces; antimicrobial peptides; and proteins and related compounds.

Embedding a bioactive agent in the silk/glycerol blend-produced film enables the delivery of active agents in a controlled released manner. Maintaining the bioactive agent in an active form throughout the process of embedding the agent in the silk enables it to be active upon release from the silk film. Controlled release of the active agent permits active agent to be released sustainably over time, with controlled release kinetics. In some instances, the bioactive agent is delivered continuously to the site where treatment is needed, for example, over several weeks. Controlled release over time, for example, over several days or weeks, or longer, permits continuous delivery of the bioactive agent to obtain preferred treatments. The controlled delivery vehicle is advantageous because it protects the bioactive agent from degradation in vivo in body fluids and tissue, for example, by proteases.

Controlled release of the active agent from the silk film may be designed to occur over time, for example, over 12 hours or 24 hours. The time of release may be selected, for example, to occur over a time period of about 12 hours to 24 hours; about 12 hours to 42 hours; or, e.g., about 12 to 72 hours. In another embodiment, release may occur for example on the order of about 1 day to 15 days. The controlled release time may be selected based on the condition treated. For example, longer times may be more effective for wound healing, whereas shorter delivery times may be more useful for some cardiovascular applications.

Controlled release of the active agent from the silk film in vivo may occur, for example, in the amount of about 1 ng to 1 mg/day. In other embodiments, the controlled release may occur in the amount of about 50 ng to 500 ng/day, or, in another embodiment, in the amount of about 100 ng/day. Delivery systems comprising therapeutic agent and a carrier may be formulated that include, for example, 10 ng to 1 mg therapeutic agent, or about 1 μg to 500 μg, or, for example, about 10 μg to 100 μg, depending on the therapeutic application.

The silk/glyerol blend-produced film of the present invention may also be surface patterned for bio-optical device application. The surface patterning technique are known in the art, for example, ink jet printing of patterns, dip pen nanolithography patterns, microcontact printing or soft lithographic techniques. See Wilran et al., 98 P.N.A.S. 13660-64 (2001); Bettinger et al, 19 Adv. Mat. 2847-50

(2007). Also see PCT/US/07/83620; PCT/US2008/082487. Topographic patterning on the surface of silk film combined with silk film's optical transparent clarity may provide high resolution surface features that are not only suitable for bio-optical device such as an optical grating, a lens, a microlen array (WO 08/127404), but also suitable for tissue engineered construct due to their ability to direct cellular function and matrix deposition such as tissue alignment and proliferation (WO 08/106485).

Hence, particular embodiments described herein provide for glycerol modified silk films that are useful for ocular biomedical devices and ocular tissue engineering. For example, in the application in corneal tissue engineering, the surface of silk film supports the corneal fibroblast attachment and proliferation. The optional surface patterning of the modified silk films provides further guidance to cell alignment. The glycerol modified silk film may be used for in vivo cornea tissue repair or in vitro cornea tissue regeneration for subsequent implantation. Because of its soft and flexible nature, the silk film modified by glycerol using the method of the present invention provides for improved comfort and compatibility to patient in need of such tissue implantation. Additional exemplary applications of modified silk film in ocular biomedical devices include, but not limited to, fabrication of soft contact lenses, intraocular lenses, glaucoma filtration implants, keratoprostheses, scleral buckles, and viscoelastic replacement agents.

Another application of the glycerol modified silk film in the present invention is to fabricate flexible optical device. As noted, silk film surface may be further patterned with high resolution features. Using the glycerol modified silk films of the present invention, a flexible, expandable holographic label may be provided that is easily elongated, stretched or deformed to match the surface contour of the product in need of, for example, a label. For example, silk film may be nanopatterned with high resolution diffraction microrelief to confer a holographic image, thus providing an edible holographic product identification label that easily conforms to a capsule, tablet, or food product. See PCT/US09/47751.

As noted herein, glycerol modified silk films are edible. Coloring agents, releasing agents, coating agents, sweetening, flavoring and perfuming agents, preservatives and antioxidants can also be present in the silk film or formulation comprising silk film. For example, a flavored silk film formulation or flavored silk film coated formulation of vitamins, nutraceuticals, or other pharmaceuticals may be produced for pediatric use.

In summary, silk films blended with glycerol (>10% w/w) are apparently enriched in α-helical structure, which further transitions to crystalline β-sheet structures upon removal of glycerol by methanol or water treatments and re-drying the film. Silk/glycerol blend films rich in β-sheet structure were composed of characteristic nano-filaments, while those rich in α-helical structure did not exhibit these morphologies. The blend films, in either the as-cast or glycerol-depleted states, were more ductile than both methanol-treated and water-annealed pure silk fibroin films, even though they were less resistant to stretch deformation. Both glycerol-blended (30% w/w) and methanol-treated silk films supported fibroblast attachment and growth. Mechanistically, the role of glycerol appears to mimic that of water in controlling the structural transitions of the silk fibroin chains, providing a new and useful control point in regulating the structure and thus material properties of silk-based biomaterials.

Thus, the embodiments of the present invention provide for a silk film comprising silk fibroin and about 10% (w/w) to about 50% (w/w) glycerol. This silk film may comprise about 20% (w/w) to about 40% (w/w), or about 30% (w/w).

Additionally, the silk film may include at least one active agent. The active agent may be cells, proteins, peptides, nucleic acid analogues, nucleotides or oligonucleotides, peptide nucleic acids, aptamers, antibodies or fragments or portions thereof, hormones, hormone antagonists, growth factors or recombinant growth factors and fragments and variants thereof, cytokines, enzymes, antibiotics or antimicrobial compounds, viruses, antivirals, toxins, prodrugs, chemotherapeutic agents, small molecules or drugs, or combinations thereof. In a particular embodiment, the active agent is a cell. The cell may be selected from hepatocytes, pancreatic Islet cells, fibroblasts, chondrocytes, osteoblasts, exocrine cells, cells of intestinal origin, bile duct cells, parathyroid cells, thyroid cells, cells of the adrenal-hypothalamic-pituitary axis, heart muscle cells, kidney epithelial cells, kidney tubular cells, kidney basement membrane cells, nerve cells, blood vessel cells, cells forming bone and cartilage, smooth muscle cells, skeletal muscle cells, oscular cells, integumentary cells, bone marrow cells, keratinocytes, pluripotent cells, induced pluripotent stem cells, adult stem cells or embryonic stem cells, or combinations thereof.

The silk film may also include silk microspheres or silk nanospheres embedded in the silk film. The silk film may be film is a layered or folded into a sponge or block. The silk films also provide for constructs for tissue engineering. In particular, the tissue engineered construct may be a corneal tissue construct in which the cell is a corneal fibroblast. In some embodiments, the silk film may further comprise a cell growth medium.

The silk films of the present invention may also include a pattern on the silk film, such as an optical pattern, in particular a holographic image.

The embodiments of the present invention also provide for a method for preparing a silk film, comprising blending a silk fibroin solution with glycerol, wherein the concentration of glycerol in the silk fibroin/glycerol blend solution is about 10% to about 50% (w/w), casting the silk fibroin/glycerol blend solution onto a film-supporting surface, and drying the silk film. The method may also include additional steps of immersing the silk film in a liquid in which glycerol dissolves for a period of time to deplete glycerol from the silk film; and drying the glycerol-depleted film. The method may also further comprise annealing the film, for example treating the film with methanol or water vapor.

The present embodiments also provide for a method of covering a surface of a substrate with a silk composition by providing a film-support substrate; and covering the film-support substrate with a silk fibroin/glycerol blend film comprising about 10% to 50% glycerol (w/w). The silk fibroin/glycerol blend film may further comprise at least one biopolymer, such as PVA or PEO. the silk fibroin/glycerol blend film may further comprise at least one active agent.

Another embodiment of the invention is a silk film-covered substrate prepared according to the method of covering a surface of a substrate with a silk composition by providing a film-support substrate; and covering the film-support substrate with a silk fibroin/glycerol blend film comprising about 10% to 50% glycerol (w/w). The substrate may be a tissue, regenerated tissue, medical device, medical implant, veterinary device, or veterinary implant, such as a dental implant. The substrate may also be a silk-based composite.

Another embodiment of the present invention is a method of embedding at least one active agent in a silk film, comprising blending a silk fibroin solution with at least one active agent and glycerol, wherein the concentration of glycerol in the silk blend solution is about 10% to 50% (w/w); casting the silk blend solution onto a film-supporting surface; and drying the film. In this method, the active agent may be cells, proteins, peptides, nucleic acid analogues, nucleotides or oligonucleotides, peptide nucleic acids, aptamers, antibodies or fragments or portions thereof, hormones, hormone antagonists, growth factors or recombinant growth factors and fragments and variants thereof, cytokines, enzymes, antibiotics or antimicrobial compounds, viruses, antivirals, toxins, prodrugs, chemotherapeutic agents, small molecules, drugs, or combinations thereof. This method may also further include the steps of immersing the silk film in a liquid in which glycerol dissolves for a period of time to deplete glycerol from the silk film; and drying the glycerol-depleted film. The method may also include the further step of annealing the film.

In some embodiments of the present invention may be defined in any of the following numbered paragraphs:

1. A silk film comprising silk fibroin and about 10% (w/w) to about 50% (w/w) glycerol.
2. The silk film of paragraph 1, wherein the glycerol content of the silk film is about 20% (w/w) to about 40% (w/w)
3. The silk film of any of paragraphs 1 to 2, wherein the glycerol content of the silk film is about 30% (w/w).
4. The silk film of any of paragraphs 1 to 3, further comprising at least one active agent.
5. The silk film of any of paragraphs 1 to 4, further comprising silk microspheres or silk nanospheres embedded in the silk film.
6. The silk film of any of paragraphs 1 to 5, wherein said film is a layered or folded into a sponge or block.
7. The silk film of any of paragraphs 1 to 6, wherein the at least one active agent is selected from the group consisting of cells, proteins, peptides, nucleic acid analogues, nucleotides or oligonucleotides, peptide nucleic acids, aptamers, antibodies or fragments or portions thereof, hormones, hormone antagonists, growth factors or recombinant growth factors and fragments and variants thereof, cytokines, enzymes, antibiotics or antimicrobial compounds, viruses, antivirals, toxins, prodrugs, chemotherapeutic agents, small molecules, drugs, and combinations thereof.
8. A construct for tissue engineering comprising the silk film of any of paragraphs 1 to 7, wherein at least one active agent is a cell.
9. The construct for tissue engineering of paragraph 8, wherein the cell is selected from the group consisting of hepatocytes, pancreatic Islet cells, fibroblasts, chondrocytes, osteoblasts, exocrine cells, cells of intestinal origin, bile duct cells, parathyroid cells, thyroid cells, cells of the adrenal-hypothalamic-pituitary axis, heart muscle cells, kidney epithelial cells, kidney tubular cells, kidney basement membrane cells, nerve cells, blood vessel cells, cells forming bone and cartilage, smooth muscle cells, skeletal muscle cells, oscular cells, integumentary cells, bone marrow cells, keratinocytes, pluripotent stem cells, induced pluripotent stem cells, adult stem cells and embryonic stem cells, and combinations thereof.
10. The construct for tissue engineering of paragraph 9, wherein the tissue engineered construct is a cornea tissue construct and the cell is corneal fibroblast.
11. The construct for tissue engineering of any of paragraphs 8 to 10, further comprising a cell growth medium.
12. The silk film of any of paragraphs 1 to 7, further comprising an optical pattern on the silk film.
13. The silk film of paragraph 12, wherein the optical pattern is a holographic image.
14. A method for preparing a silk film, comprising:
    blending a silk fibroin solution with glycerol, wherein the concentration of glycerol in the silk fibroin/glycerol blend solution is about 10% to about 50% (w/w);
    casting the silk fibroin/glycerol blend solution onto a film-supporting surface; and drying the silk film.
15. The method of paragraph 14, further comprising the steps of immersing the silk film in a liquid in which glycerol dissolves for a period of time to deplete glycerol from the silk film; and drying the glycerol-depleted film.
16. The method of paragraphs 14 or 15, further comprising annealing said film.
17. A method for covering a surface of a substrate with a silk composition comprising:
    providing a film-support substrate; and
    covering the film-support substrate with a silk fibroin/glycerol blend film comprising about 10% to 50% glycerol (w/w).
18. The method of paragraph 17, wherein the silk fibroin/glycerol blend film further comprises at least one biopolymer.
19. The method of paragraph 18, wherein the biopolymer is PVA or PEO.
20. The method of paragraph 19, wherein the silk fibroin/glycerol blend film further comprises at least one active agent.
21. A silk film-covered substrate prepared according to the method of paragraphs 17-20.
22. The silk film-covered substrate of paragraph 21, wherein the substrate is a tissue, regenerated tissue, medical device, medical implant, veterinary device, or veterinary implant.
23. The silk film-covered substrate of paragraphs 20 or 22, wherein the substrate is a silk-based composite.
24. A method of embedding at least one active agent in a silk film, comprising: blending a silk fibroin solution with at least one active agent and glycerol, wherein the concentration of glycerol in the silk blend solution is about 10% to 50% (w/w); casting the silk blend solution onto a film-supporting surface; and drying the film.
25. The method of paragraph 24, wherein the at least one active agent is selected from the group consisting of cells, proteins, peptides, nucleic acid analogues, nucleotides or oligonucleotides, peptide nucleic acids, aptamers, antibodies or fragments or portions thereof, hormones, hormone antagonists, growth factors or recombinant growth factors and fragments and variants thereof, cytokines, enzymes, antibiotics or antimicrobial compounds, viruses, antivirals, toxins, prodrugs, chemotherapeutic agents, small molecules, drugs, and combinations thereof.
26. The method of paragraph 24 or 25, further comprising the steps of immersing the silk film in a liquid in which glycerol dissolves for a period of time to deplete glycerol from the silk film; and drying the glycerol-depleted film.
27. The method of any of paragraphs 24 to 26, further comprising annealing said film.

EXAMPLES

Example 1. Silk Fibroin Purification

Silk fibroin aqueous stock solutions were prepared as previously described. Sofia et al., 54 J. Biomed. Mater. Res.

139-48 (2001). Briefly, cocoons of *Bombyx mori* were boiled for 20 min in an aqueous solution of 0.02 M sodium carbonate, and then rinsed thoroughly with pure water. After drying, the extracted silk fibroin was dissolved in 9.3 M LiBr solution at 60° C. for 4 hr, yielding a 20% (w/v) solution. This solution was dialyzed against distilled water using SLIDE-A-LYZER® Dialysis Cassettes, 3,500 MWCO (Pierce, Rockford, Ill.) for 3 days to remove the salt. The solution was optically clear after dialysis and was centrifuged to remove the small amounts of silk aggregates that formed during the process, usually from environment contaminants that are present on the cocoons. The final concentration of silk fibroin aqueous solution was approximately 6% (w/v). This concentration was determined by weighing the residual solid of a known volume of solution after drying.

The 6% silk fibroin solution was stored at 4° C. before use and may be diluted to a lower concentration with ultrapure water. To obtain a silk fibroin solution with a higher concentration, the 6% silk fibroin solution may be dialyzed against a hygroscopic polymer, such as polyethylene glycol (PEG), amylase, or sericin. For example, a 6% silk fibroin solution may be exposed to a 25%-50% wt % PEG (MW 8,000 to 10,000) solution on the outside of a SLIDE-A-LYZER® 3,500 MWCO Dialysis Cassettesfor 2 to 12 hr by osmotic pressure, and the final concentration of aqueous silk solution concentrated to between 8%-30% wt % or greater.

Example 2. Preparation of Silk/Glycerol Blend Films

The purified silk fibroin solution was mixed with glycerol at weight ratios of 0%, 5%, 10%, 20%, 30%, 40%, 50% (w/w). The mixed solutions were poured into Petri dishes and dried at room temperature in a laminar flow hood overnight. Unless otherwise stated, the 'dry blend films' refers to the films prepared by this direct casting and overnight drying, and the 'wet blend films' refers to the same cast and dried films from which the glycerol is subsequently extracted in ultrapure water at 37° C. for 1 hr, after which the films are dried again in the air. For additional variables in the treatment groups, methanol treatments were used, and in these cases the films (with and without glycerol) were immersed in 90% (v/v) methanol for 1 hr and then air-dried.

Example 3. Dissolution of Silk/Glycerol Films

Blend films were cut into approximately 5 mm×5 mm squares, and one square film was weighed and immersed in ultrapure water in a 2 ml tube to a concentration of 1% (weight of film/volume of water), and kept at 37° C. for 1 hr or 1 day. After the incubation, the silk films were removed from the solution, air-dried overnight, weighed, and compared with the mass of original film to obtain residual mass (%). The remaining solution was subjected to UV absorbance measurement at 280 nm. The absorbance values were converted to the amount of silk solubilized in water using purified silk fibroin solution at various concentrations as standards. The amount of dissolved silk was then compared with the total silk mass in the film to obtain the percentage of the film dissolved silk in water.

Example 4. Analysis of Silk/Glycerol Films by Fourier Transform Infrared (FTIR) Spectroscopy The secondary structures present in the films, including random coil, alpha-helices, beta-pleated sheets and turns, were evaluated using Fourier Self-Deconvolution (FSD) of the infrared absorbance spectra. FTIR analysis of treated samples was performed with a Bruker Equinox 55/S FTIR spectrometer (Bruker Optics Inc., Billerica, Mass.), equipped with a deuterated triglycine sulfate detector and a multiple-reflection, horizontal MIRacle® ATR attachment with a Germanium (Ge) crystal, from Pike Tech. (Madison, Wis.). A 5 mm×5 mm square-shape silk film was placed in the Ge crystal cell and examined with the FTIR microscope in the reflection mode. Background measurements were taken with an empty cell and subtracted from the sample reading. For each measurement, sixty-four scans were recorded with a resolution of 4 $cm^{-1}$, and the wavenumber ranged from 400 $m^{-1}$ to 4000 $cm^{-1}$.

FSD of the infrared spectra covering the amide I region (1595 $cm^{-1}$-1705 $cm^{-1}$) was performed by Opus 5.0 software (Opus Software, Inc., San Francisco, Calif.) as previously described. Hu et al., 39 Macromolecules, 6161-70 (2006). Absorption bands in the frequency range 1616 $cm^{-1}$-1637 $cm^{-1}$ and 1695 $cm^{-1}$-1705 $cm^{-1}$ represented enriched β-sheet structure; bands in the range 1638 $cm^{-1}$-1655 $cm^{-1}$ were ascribed to random coil structure; bands in the range 1656 $cm^{-1}$-1663 $cm^{-1}$ ascribed to alpha-helices; and bands in the range 1663 $cm^{-1}$-1695 $cm^{-1}$ to turns. Id.

Example 5. Mechanical Properties of Silk/Glycerol Films

Tensile tests were performed on an Instron 3366 testing frame equipped with a 10 N capacity load cell and BIO-PULS™ testing system (Instron®, Norwood, Mass.), including submersible pneumatic clamps and temperature-controlled liquid bath. Film samples were cast into silicone molds based on ASTM standard D638-02a, and scaled up 2×, resulting in an overall length of 80 mm to accommodate the large surfaces needed for clamping and gauge length necessary for video extensometry (28 mm). For a dry environment, the films were conditioned in an environmental chamber at 25° C. and 50% relative humidity for two days. For a wet environment, the silk/glycerol film samples were hydrated in 0.1 M phosphate buffered saline (PBS) for 1 hr, and then submerged in a BIOPULS™ bath (37±0.3° C.) filled with PBS for at least 5 min prior to testing. The pure silk fibroin films (0% glycerol) were pre-treated with 90% v/v methanol for 1 hr, and then treated in the same way as glycerol samples. All films were tested at a strain control rate of 0.1% $s^{-1}$, based on the initial clamp-to-clamp length (nominal length ~47 mm, nominal elongation rate ~2.82 mm/min). Load and video extensometer strain data were captured at 20 Hz., the latter based on two fiducial painted markers placed at a nominal distance of ~1 cm on the surface of the thinnest portion of each film. Five replicates of each film were tested. The original cross sectional area was determined by measuring the film thickness by SEM and multiplying by the specimen width (10 mm). The nominal stress and strain were graphed, and the initial "linear elastic modulus", strain to failure, and ultimate tensile strength (UTS) were determined. UTS was determined as the highest stress value attained during the test. The initial "linear elastic modulus" was calculated by using a least-squares' fitting between the point corresponding to 0.1 N load and the point corresponding to 50% of the UTS. This was deemed sufficient to objectively capture the linear portion of the stress/strain curve for all samples tested. The elongation to failure was determined as the last data point before a >10% decrease in load.

Example 6. Scanning Electron Microscopy (SEM)

Silk films were fractured in liquid nitrogen and sputtered with platinum. The cross-section and surface morphologies of the different silk films were imaged using a Zeiss SUPRA™ 55 VP SEM (Carl Zeiss, Inc., Jena, Germany).

Example 7. Fibroblast Culture and Adhesion on Silk Films

Fibroblast cells were expanded in a growth medium containing 90% DMEM, 10% fetal bovine serum (FBS), 100 U/ml penicillin, 1000 U/ml streptomycin. Cell cultures were maintained at 37° C. in an incubator with 95% air and 5% $CO_2$. The cultures were replenished with fresh medium at 37° C. every two days. For adhesion, cells were seeded on silk films that were pre-cast in 24-well plates with 50,000 cells per well in 1 ml of serum-containing medium. Empty wells with tissue culture plastic (TCP) and no silk served as controls. Cell attachment was evaluated 3 hr after cell seeding by adding 50 µl of alamar blue to the culture medium, culturing for another 6 hr, and determining the medium fluorescence (Ex=560 nm, Em=590 nm). During the culture, cell proliferation was determined using alamar blue staining and cell morphology was monitored by phase contrast light microscopy (Carl Zeiss, Inc., Jena, Germany).

All experiments were performed with a minimum of N=3 for each data point. Statistical analysis was performed by one-way analysis of variance (ANOVA) and Student-Newman-Keuls Multiple Comparisons Test. Differences were considered significant when $p \leq 0.05$, and very significant when $p \leq 0.01$.

We claim:

1. A silk fibroin/glycerol blend film comprising:
   silk fibroin characterized by beta sheet secondary structure, wherein at least 40% of the silk fibroin in the film is present in beta sheet form; and
   glycerol, wherein the glycerol content is 20% (w/w) to 50% (w/w) of the film,
   wherein the silk fibroin/glycerol blend film is characterized by optical transparent clarity.

2. The silk fibroin/glycerol blend film of claim 1, wherein the glycerol content is 20% (w/w) to 40% (w/w) of the film.

3. The silk fibroin/glycerol blend film of claim 1, wherein the glycerol content is 30% (w/w) of the film.

4. The silk fibroin/glycerol blend film of claim 1, further comprising at least one active agent.

5. The silk fibroin/glycerol blend film of claim 4, wherein the at least one active agent is selected from the group consisting of cells, proteins, peptides, nucleic acid analogues, nucleotides or oligonucleotides, peptide nucleic acids, aptamers, antibodies or fragments or portions thereof, hormones, hormone antagonists, growth factors or recombinant growth factors and fragments and variants thereof, cytokines, enzymes, antibiotics or antimicrobial compounds, viruses, antivirals, toxins, prodrugs, chemotherapeutic agents, small molecules, drugs, and combinations thereof.

6. A construct for tissue engineering comprising the silk fibroin/glycerol blend film of claim 4, wherein the at least one active agent is a cell.

7. The construct for tissue engineering of claim 6, wherein the cell is selected from the group consisting of hepatocytes, pancreatic Islet cells, fibroblasts, chondrocytes, osteoblasts, exocrine cells, cells of intestinal origin, bile duct cells, parathyroid cells, thyroid cells, cells of the adrenal-hypothalamic-pituitary axis, heart muscle cells, kidney epithelial cells, kidney tubular cells, kidney basement membrane cells, nerve cells, blood vessel cells, cells forming bone and cartilage, smooth muscle cells, skeletal muscle cells, ocular cells, integumentary cells, bone marrow cells, keratinocytes, pluripotent stem cells, induced pluripotent stem cells, adult stem cells and embryonic stem cells, and combinations thereof.

8. The construct for tissue engineering of claim 7, wherein the construct for tissue engineering is a cornea tissue construct and the cell is a corneal fibroblast.

9. The construct for tissue engineering of claim 6, further comprising a cell growth medium.

10. The silk fibroin/glycerol blend film of claim 1, further comprising silk microspheres or silk nanospheres embedded in the silk film.

11. The silk fibroin/glycerol blend film of claim 1, wherein said film is layered or folded into a sponge or block.

12. The silk film of claim 1, further comprising an optical pattern on the silk fibroin/glycerol blend film.

13. A silk fibroin/glycerol blend film of claim 1, prepared by a method comprising:
    blending a silk fibroin solution and glycerol to form a silk fibroin/glycerol blend solution;
    casting the silk fibroin/glycerol blend solution; and
    drying the cast solution.

14. A film comprising silk fibroin blend with glycerol,
    wherein at least 40% of the silk fibroin in the film is present in beta sheet form; and
    wherein the glycerol content is 20% (w/w) to 50% (w/w) of the film,
    wherein the film is characterized by optical transparent clarity.

* * * * *